United States Patent [19]
Brufani et al.

[11] Patent Number: 5,352,810
[45] Date of Patent: Oct. 4, 1994

[54] PHOSPHATIDYLINOSITOL ANALOGUES, INHIBITORS OF PHOSPHATIDYLINOSITOL SPECIFIC PHOSPHOLIPASE C

[75] Inventors: Mario Brufani, Castelgandolfo; Maria Candida Cesta, Rome; Enrico Ferrari, Sesto San Giovanni; Luigi Filocamo; Sperandina Lappa, both of Rome; Stefano Maiorana, Milan; Pier Giuseppe Pagella, Isola San Antonio, all of Italy

[73] Assignee: Mediolanum Farmaceutici S.P.A., Milan, Italy

[21] Appl. No.: 824,318

[22] Filed: Jan. 23, 1992

[30] Foreign Application Priority Data

Feb. 1, 1991 [IT] Italy .................... MI91A000251

[51] Int. Cl.$^5$ ............................. C07F 9/02
[52] U.S. Cl. ......................... 554/79; 554/154
[58] Field of Search ........... 554/79, 154; 514/143, 514/148, 886

[56] References Cited

PUBLICATIONS

Hendrickson et al., Bioorganic & Medicinal Chemistry Letters, vol. #11, pp. 615–618, 1991.
Word et al., Tetrahedron Letters, vol. 29, #46, pp. 6013–6016, 1988.

Primary Examiner—José G. Dees
Assistant Examiner—Deborah D. Carr
Attorney, Agent, or Firm—Oliff & Berridge

[57] ABSTRACT

Phosphatidylinositol analogues, inhibitors of phosphatidylinositol-specific phospholipase C of general formula (I)

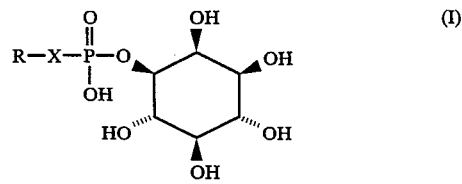

wherein X and R have the meanings specified in the description, suitable for preparing pharmaceutical compositions for the treatment of tumoral, thrombotic and inflammatory type pathologies.

6 Claims, 1 Drawing Sheet

PHOSPHATIDYLINOSITOL ANALOGUES, INHIBITORS OF PHOSPHATIDYLINOSITOL SPECIFIC PHOSPHOLIPASE C

Phosphatidylinositol specific phospholipase C (PLC) is the enzyme which, inside the cellular membrane, as a consequence of the activation operated by various neurotransmitters, hormones, and growth factors acting on specific membrane receptors, hydrolyzes phosphatidylinositol-4,5-diphosphate, thereby producing diacylglycerol and inositol-1,4,5-triphosphate.

Inositol-1,4,5-triphosphate and diacyl-glycerol play inside the cell the role of second messengers, the first one by mobilizing calcium from intracellular depots and the second one by activating the phosphorylating enzyme Kinase C. Therefore PLC plays an essential role in many cellular activation processes induced by neurotransmitters, hormones and growth factors.

Recent researches evidenced that several oncogeni carry out their action encoding proteins which, acting as regulation factors of the complex process of the membrane phosphoinositides metabolism, alter the biochemical equilibria regulating said process in non pathosis, therefore becoming determinant factors in some forms of cancer.

The hypothesis was thus put forward according to which phosphoinositides metabolism slowdown, obtained by inhibiting the key-enzyme of said process could be translated into an antitumoral action. In addition it is known that thrombin carries out an aggregating action, by activating a specific receptor present in platelets membranes, which on its turn activates PLC and the phosphoinositides cycle.

Finally it is known that the diacylglicerol released from PLC acts as a substrate of lipase enzymes, being able to remove from said compound arachidonic acid, which acting as a substrate of cyclooxygenase and lipooxygenase enzymes, forms prostaglandin thromboxanes leukotrienes, having a fundamental biochemical function in the genesis and in the amplification of the inflammatory processes. Consequently specific PLC inhibitors could be used as antitumoral, platelets antiaggregating and antiinflammatory drugs.

SUMMARY

The present invention regards a series of phosphatidylinositol analogues able to inhibit phosphatidylinositol-specific phospholipase C.

Object of the present invention are also the synthesis process of said compounds and pharmaceutical formulations containing them as active ingredients.

Said phosphatidylinositol analogues have the following general formula (I)

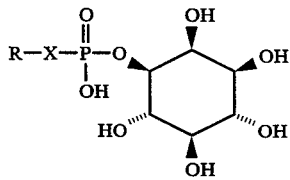

wherein X is S or O and R has one of the following meanings:

1) a linear or branched alkyl radical having from 4 to 30 carbon atoms preferably it is a $C_8$–$C_{20}$ alkyl radical, such as octyl, tetradecyl, hexadecyl, octadecyl, eicosyl;

2) an arylalkyl radical wherein the alkyl portion has from 1 to 10 carbon atoms, such as benzyl, phenylethyl, naphthylethyl, phenylpropyl, phenylhexyl;

3) 2,3 diacyloxypropyl:

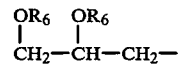

wherein $R_6$ is a higher saturated or unsaturated acyl radical, in particular stearoyl, palmitoyl, linoleyl, linolenyl, oleyl, myristoyl, lauroyl;

4) 2,3 dialkyloxypropyl:

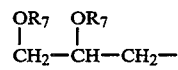

wherein $R_7$ is a higher saturated or unsaturated alkyl radical, particularly stearyl, palmityl, oleyl, myrystyl, cetyl;

5) 2,3 alkylacyloxypropyl:

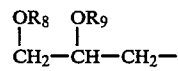

wherein $R_8$ is a higher saturated or unsaturated alkyl radical, in particular stearyl, palmityl, oleyl, myristyl, cetyl; $R_9$ is a short chain acyl group and in particular acetyl;

6) an alkyl radical containing a carbonyl group of formula:

wherein $R_{10}$ has the same meaning as R at item 1, Z=O, NH, n ranges from 2 to 6.

7) an alkyl radical containing a carbonyl group of formula:

wherein $R_{10}$ has the same meaning as R at item 5, Y=O, NH, S and m ranges from 1 to 6.

The process for preparing the compounds of general formula (I) wherein X=S is characterized in that:
a) diethylphosphothiolate having the general formula (II) is prepared

b) phosphothiolate (II) is transesterified by a treatment with thrymethylsilylbromide;
c) the transesterified product obtained in step b) is treated with myoinositol protected at the hydroxyl groups 2,3,4,5 and 6 in the presence of a condensing agent;
d) the protecting groups are removed in the transesterified product coming from step c) thereby restoring the hydroxy groups 2,3,4,5 and 6.

In a similar way the compounds of general formula (I) wherein X=O are prepared, by preparing in the step a) the phosphoric triester having the formula:

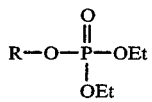
(II)

DETAILED DESCRIPTION OF THE INVENTION

Figure 1:
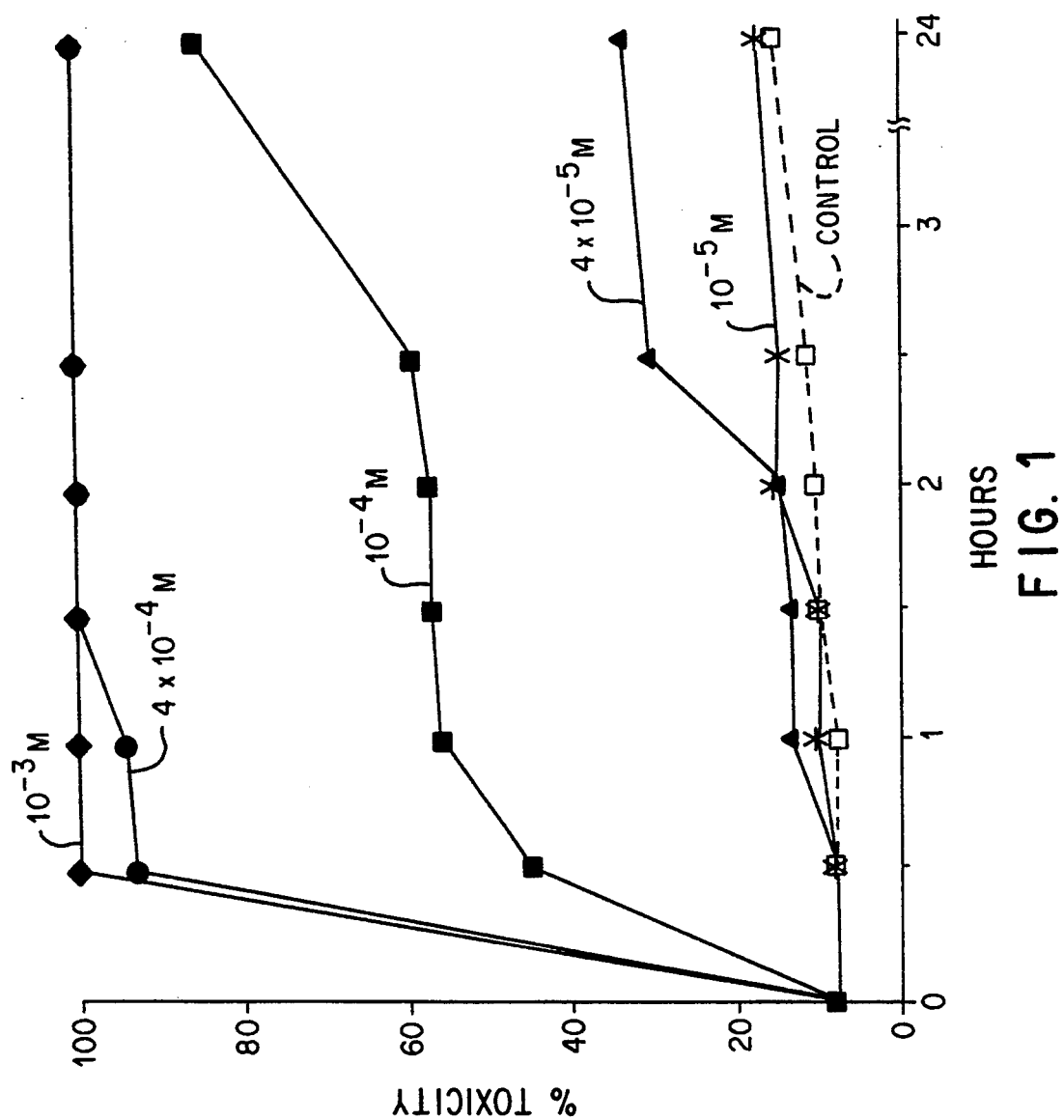

The characteristics and advantages of the phosphatidylinositol analogues, of the process for their preparation and of their use as inhibitors of phosphatidylinositol specific phospholipase C will be better illustrated in the course of the following detailed description.

The phosphatidylinositol analogues of the present invention have the following general formula (I)

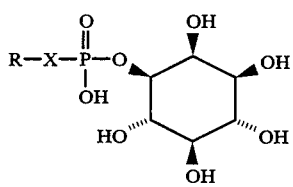
(I)

wherein X means S or O and R has one of the following meanings:

1) a linear or branched alkyl radical having from 4 to 30 carbon atoms preferably it is a $C_6$-$C_{20}$ alkyl radical, such as octyl, tetradecyl, hexadecyl, octadecyl, eicosyl;

2) an arylalkyl radical wherein the alkyl portion has from 1 to 10 carbon atoms, such as benzyl, phenylethyl, naphthylethyl, phenylpropyl, phenylhexyl;

3) 2,3 diacyloxypropyl:

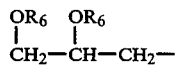

wherein $R_6$ is higher saturated or unsaturated acyl radical, in particular stearoyl, palmitoyl, oleyl, linoleyl, linolenyl, myristoyl, lauroyl;

4) 2,3 dialkyloxypropyl:

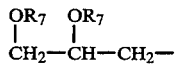

wherein $R_7$ is a higher saturated or unsaturated alkyl radical, particularly stearyl, palmityl, oleyl, myrystyl, cetyl;

5) 2,3 alkylacyloxypropyl:

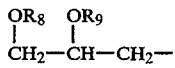

wherein $R_8$ is a higher saturated or unsaturated alkyl radical in particular stearyl, palmityl, oleyl, myristyl, cetyl; $R_9$ is a short chain acyl group and in particular acetyl;

6) an alkyl radical containing a carbonyl group of formula:

$$R_{10}-COZ(CH_2)_n-$$

wherein $R_{10}$ has the same meaning as R at item 1, Z=O, NH, n ranges from 2 to 6.

7) an alkyl radical containing a carbonyl group of formula:

$$R_{10}-YCO(CH_2)_m-$$

wherein $R_{10}$ has the same meaning as R at item 5, Y=O, NH, S and m ranges from 1 to 6.

The process for preparing the compounds of general formula (I) having X=S encompasses a first step in which diethyl phosphothiolate having the general Formula (II) is prepared

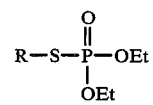
(II)

The preparation methods of said intermediate product described later-on, differ as a function of the various meanings of R above mentioned.

Phosphothiolate (II) is then transesterified with trimethylsilylbromide in an organic solvent, preferably $CH_2Cl_2$, under inert gas atmosphere, at room temperature, by using a molar ratio of timethylsilylbromide : phosphothiolate comprised between 2.5 and 4.5.

The obtained transesterified product is reacted with myo-inositol protected at the hydroxyl groups 2,3,4,5 and 6 with protecting groups such as benzyl, allyl, trialkylsilyl, alkylarylsilyl, tetrahydropyranyl, acetone, cyclohexylidene, acetyl, propanoyl, butirryl, pentanoyl, in the presence of a condensing agent such as substituted or not substituted benzenesulphonyl chloride or pivaloyl chloride.

This reaction is carried out in pyridine and triethylamine and optionally also $CHCl_3$ ambient under inert gas atmosphere at room temperature with a molar ratio myo-inositol : phosphothiolate comprised between 0.8 and 2.0.

The protecting groups of myo-inositol phosphothiolate thus obtained are removed according to one of the following methods:

1) with boron trifluoride etherate and ethylmercaptan in the case of benzylethers;

2) by using palladium on carbon and p-toluensulphonic acid as the catalyst in protic solvents in the case of allylethers;

3) by mild acid hydrolysis with hydrochloric acid or trifluoroacetic acid in the case of tetrahydropyranyl, acetonide, cyclohexylidene groups.

4) by using tetrabutylammonium fluoride or by acid hydrolysis with hydrochloric acid or acetic acid in the case of trialkylsilyl or alkylarylsilyl groups;

5) by mild basic hydrolysis or by a reaction with hydrazine in the case of shortchain acylesters.

In case 1) the reaction is carried out in $CHCl_3$ under inert gas atmosphere by using an amount ranging from 15 to 25 ml of ethylmercaptan and from 3 to 5 ml of boron trifluoride etherate per mMol of myo-inositol derivative.

In case R is an alkyl or an arylalkyl radical the corresponding phosphothiolates are prepared by reacting the corresponding mercaptans with n-butyllithium and diethylchlorophosphate under nitrogen atmosphere.

In case R is a dialkyloxypropyl:

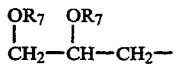

the corresponding phosphothiolates are obtained by alkylating hydroxyl groups of thioglycerol which was previously protected at the mercapto-group.

In case R is an alkyl containing in its chain an ester or an amide group of the type:

a suitable disulphide is reacted with thionylchloride and $(Me_3SiO)_3P$ or with N-bromosuccinimide or N-bromophtalimide thereby giving the corresponding thioimides by which the corresponding phosphothiolates are obtained after the reaction with $(EtO)_3P$ (triethyl phosphite). The starting disulphide is prepared in the case of the esters, by esterifying a bis(alkylalcohol)-disulphide with an acylchloride according to known methods.

In the case of amides, the starting disulphide is prepared by acylating a bis(alkylamine)disulphide.

In case R is an alkyl containing in its chain an ester, a thioester or an amide group of the type:

by corresponding phosphothiolates are prepared by firstly acylating an alcohol, a mercaptan or an amine with a mercaptoalkylcarboxilic acid, which was previously protected at the thiogroup, then removing said protecting group and subjecting the compound obtained to the reaction with thionylchloride and $(Me_3SiO)_3P$ as above described, or by reacting the mercaptan (or its corresponding disulphide) with N-bromosuccinimide or N-bromophtalimide, thereby giving the corresponding thioimides which are then reacted with $(EtO)_3P$ (triethylphosphite). When necessary the thiogroup is protected by transforming it into a benzil-thioether, using as the reactant benzylchloride, or by means of an oxidation to the corresponding disulphide using as the oxidizing agent ferric chloride.

By a similar process the compounds of general formula (I) wherein X=O are prepared, by preparing in the first step the phosphoric triester having the formula

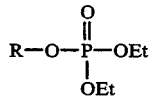

The following examples of the present invention are reported hereinbelow only for illustrative purposes.

EXAMPLE 1

1.1 DIETHYL OCTADECYLPHOSPHOTHIOLATE 6.25 ml (10 mMol) of n-butyl-lithium (n-BuLi) in hexane (1.6 M) were added slowly to a solution of 2.86 g (10 mMol) of 1-octadecylmethylmercaptan in 10 ml of anhydrous THF, under stirring at 0° C. and under $N_2$ atmosphere. The formation of a white precipitate was observed. After 30' at room temperature, 1.44 ml (10 mMol) of diethyl chlorophosphate were slowly added. After resolubilizing completely the precipitate, the solution was maintained under stirring for 1 h, then 5 ml of water were added and the resulting mixture was extracted with diethylether.

The ethereal extracts were dried on $Na_2SO_4$ and the solvent was evaporated under reduced pressure thereby obtaining a colourless oil which was purified on a chromatographic column of silica gel (Merck n. 7734), using as the eluent a mixture of hexane/ethyl acetate 6:4. 3.67 g (8.7 mMol) of an oily product were obtained.

The yield was 87%.

Analysis: $C_{22}H_{47}O_3PS$ (C,H).

$^1$H-NMR (80 MHz, $CDCl_3$): δ0.83 (m,9H), 1.25(m,30H), 1.50(m,2H), 2.75(t,2H), 4.15(q,4H) ppm.

1.2 1-O-(OCTADECYLPHOSPHOTHIOLYL)-2,3,4,5,6-PENTA-O-BENZYL-MYO-INOSITOL 1 ml (7.3 mMol) of trimethylsilylbromide were added to a solution of 1.029 g (2.43 mMol) of diethyloctadecylphosphothiolate in 1 ml of anhydrous $CH_2Cl_2$, under stirring and under $N_2$ atmosphere.

The obtained solution was maintained for 6 h at room temperature, then the solvent was evaporated under reduced pressure and a mixture of 4 ml of anhydrous pyridine and 3 ml of anhydrous $CHCl_3$ were added. 2 ml (14.4 mMol) of triethylamine, 1.4 g (2.2 mMol) of D,L 2,3,4,5,6-penta-O-benzyl-myo-inositol and 2.94 g (9.72 mMol) of triisopropylbenzensulphonylchloride (TiPSCl) were added to this solution under stirring and under $N_2$ atmosphere.

After 48 h 10 ml of $H_2O$ were added and the mixture was left for 30' after that it was acidified with a solution 0.5 M of citric acid and extracted with $CHCl_3$.

The organic extracts were washed with a citric acid solution, then with water, finally dried on $Na_2SO_4$ and the solvent was evaporated under reduced pressure.

Obtained were 3.80 g of a brown oil which was purified by using a chromatographic column of silica gel (Merck n. 7734).

The elution was carried out with the following gradient: chloroform, chloroform-methanol 96:4, chloroform-methanol 9:1. 1.36 g (1.39 mMol) of an oil were obtained with a yield of 57%.

Analysis: $C_{59}H_{79}O_8PS$ (C,H).

$^1$H-NMR (200 MHz, $CDCl_3$): δ0.82(t,3H), 1.25(m,30H), 1.60(m,2H), 2.75(t,2H), 3.53(m,4H), 4.04(m,2H), 4.78(m,10H), 7.26(m,25H) ppm.

1.3 1-O-(OCTADECYLPHOSPHOTHIOLYL)-MYO-INOSITOL.

5 ml of ethylmercaptan and 1.1 ml of boron trifluoride etherate were added to a solution of 270 mg (0.28 mMol) of 1-O-(octadecylphosphothiolyl)-2,3,4,5,6-penta-O-benzyl-myo-inositol in 5 ml of anhydrous $CHCl_3$ under stirring and under $N_2$ atmosphere. The resulting mixture was maintained at room temperature for 1 h, thereafter 5 ml of $H_2O$ were added and the resulting mixture was washed with ether, the aqueous phase was recovered and evaporated under reduced pressure while maintaining the water temperature at 25° C. The white precipitate formed was filtered, washed with water and dried with the aid of vacuum at room temperature. 48 mg (0.091 mMol of a white solid were obtained (yield 33%)

Analysis: $C_{24}H_{49}O_8PS$ (C,H).

$^1$H-NMR (200 MHz, DMSO): δ0.83(t,BH), 1.25 (m,30H), 1.55(m,2H), 2.70 (m,2H), 2.93(t,1H), 3.12(dd,1H), 3.42(t,1H), 3.52(t,1H), 3.66(m,2H) ppm.

EXAMPLE 2

2.1 DIETHYL HESADECYLPHOSPHOTHIOLATE 6.25 ml (10 mMol) of nBuLi dissolved in hexane (1.6 M) were slowly added to a solution of 2.58 g (10 mMol) of 1-hexadecylmercaptan in 10 ml of anhydrous THF under stirring at 0° C. and under $N_2$ atmosphere.

The formation of a white precipitate was observed.

After 30 minutes at room temperature 1.44 ml (10 mMol) of diethyl chlorophosphate were slowly added.

After resolubilizing completely the precipitate, the solution was maintained under stirring for 1 h, then 5 ml of $H_2O$ were added and the mixture was extracted with diethyl ether. The ethereal extracts were dried on $Na_2SO_4$ and the solvent was evaporated under reduced pressure, thereby obtaining a colourless oil which was purified on a chromatographic column of silica gel (Merck n. 7734) by using as the eluent a mixture of hexane/ethyl acetate 6:4. 3.47 g (8.8 mMol) of an oily product were obtained. (yield 88%).

Analysis: $C_{20}H_{43}O_3PS$ (C,H).

2.2 1-O-(HEXADECYLPHOSPHOTHIOLYL)-2,3,4,5,6-PENTA-O-BENZYL-MYO-INOSITOL 1 ml (7.3 mMol) of trimethylsilyl bromide were added to a solution of 0.96 g (2.43 mMol) of diethylhexadecylphosphothiolate in 1 ml of anhydrous $CH_2Cl_2$ under stirring and under $N_2$ atmosphere.

The mixture was kept at room temperature for 6 h, afterwards the solvent was evaporated under reduced pressure and a mixture consisting of 4 ml of anhydrous pyridine and 3 ml of anhydrous $CHCl_3$ was added.

2 ml (14.4 mMol) of triethylamine, 1.4 g (2.2 mMol) of D,L,2,3,4,5,6-penta-O-benzyl-myo-inositol and 2.94 g (9.72 mMol) of triisopropylbenzensulfonyl chloride (TiPSCl) were added to this solution under stirring and under $N_2$ atmosphere.

After 48 h 10 ml of $H_2O$ were added and the solution was left for 30', after that it was acidified by means of a 0.5 M citric acid solution and extracted with $CHCl_3$. The organic extracts were washed at first with a citric acid solution, then with water, finally dried on $Na_2SO_4$ and the solvent was evaporated under reduced pressure. 3.70 g were obtained of a brown oil which was subsequently purified on a chromatographic column of silica gel (Merck n. 7734). The elution was carried out with the following gradient: chloroform, chloroform-methanol 96:4, chloroformmethanol 9:1.

Obtained were 1.100 g (1.16 mMol) of an oil with a yield of 47.7%

Analysis: $C_{57}H_{75}O_8PS$ (C,H).

2.3 1-O-(HEXADECYLPHOSPHOTHIOLYL)-MYO-INOSITOL 20 ml of ethylmercaptan and 44 ml of borontrifluoride etherate were added under stirring and under $N_2$ atmosphere to a solution of 800 mg (0.84 mMol) of 1-O-(hexadecylphosphothiolyl)-2,3,4,5,6-penta-O-benzyl-myo-inositol in 20 ml of anhydrous $CHCl_3$. The solution was maintained at room temperature for 1 h, then 20 ml of $H_2O$ were added and the mixture was washed with ether, the aqueous phase was collected and evaporated under reduced pressure while maintaining the water temperature at 25° C.

The white precipitate was filtered, washed with water and dried under vacuum at room temperature. Obtained were 72 mg (0.14 mMol) of a white solid (yield 17%)

Analysis: $C_{22}H_{45}O_8PS$ (C,H).

EXAMPLE 3

3.1 DIETHYL TETRADECYLPHOSPHOTHIOLATE 6.25 ml (10 mMol) of nBuLi dissolved in hexane (1.6 M) were slowly added to a solution of 2.30 g (10 mMol) of 1-tetradecylmercaptan in 10 ml of anhydrous THF under stirring at 0° C. and under $N_2$ atmosphere.

The formation of a white precipitate was observed.

After 30 minutes at room temperature 1.44 ml (10 mMol) of diethyl chlorophosphate were slowly added.

After resolubilizing completely the precipitate, the solution was maintained under stirring for 1 h, then D ml of $H_2O$ were added and the mixture was extracted with diethyl ether. The ethereal extracts were dried on $Na_2SO_4$ and the solvent was evaporated under reduced pressure, thereby obtaining a colourless oil which was purified on a chromatographic column of silica gel (Merck n. 7734) by using as the eluent a mixture of hexane/ethyl acetate 6:4. 3.14 g (8.6 mMol) of an oily product were obtained. The yield was 86%.

Analysis: $C_{18}H_{39}O_3PS$ (C,H).

3.2 1-O-(TETRADECYLPHOSPHOTHIOLYL)-2,3,4,5,6-PENTA-O-BENZYL-MYOINOSITOL 1 ml (7.3 mMol) of trimethylsilyl bromide were added to a solution of 0.9 g (2.43 mMol) of diethyltetradecylphosphothiolate in 1 ml of anhydrous $CH_2Cl_2$ under stirring and under $N_2$ atmosphere.

The obtained solution was maintained for 6 h at room temperature, afterwards the solvent was evaporated under reduced pressure and a mixture consisting of 4 ml of anhydrous pyridine and 3 ml of anhydrous $CHCl_3$ was added.

2 ml (14.4 mMol) of triethylamine, 1.4 g (2.2 mMol) of D,L-2,3,4,5,6-penta-O-benzyl-myo-inositol and 2.94 g (9.72 mMol) of triisopropylbenzensulfonyl chloride (TiPSCl) were added to this solution under stirring and under $N_2$ atmosphere.

After 48 h 10 ml of $H_2O$ were added and the solution was left for 30', after that it was acidified by means of a 0.5 M citric acid solution and extracted with $CHCl_3$. The organic extracts were washed at first with a citric acid solution, then with water, finally dried on $Na_2SO_4$ and the solvent was evaporated under reduced pressure. 3.55 g were obtained of a brown oil which was subsequently purified on a chromatographic column of silica gel (Merck n. 7734). The elution was carried out with the following gradient; chloroform, chloroform-methanol 96:4, chloroformmethanol 9:1.

Obtained were 1.2 g (1.30 mMol) of an oil with a yield of 54%.

Analysis: $C_{55}H_{71}O_8PS$ (C,H).

3.3 1-O-(TETRADECYLPHOSPHOTHIOLYL)-MYO-INOSITOL 20 ml of ethylmercaptan and 4.4 ml of boron trifluoride etherate were added to a solution of 756 mg (0.84 mMol) of 1-O-(tetradecylphosphothiolyl)- 2,3,4,5,6-penta-O-benzyl-myo-inositol in 20 ml of anhydrous $CHCl_3$ under stirring and under $N_2$ atmosphere. The solution was maintained at room temperature for 1 h, then 20 ml of $H_2O$ were added and the mixture was washed with ether, the aqueous phase was collected and evaporated under reduced pressure while maintaining the water temperature at 25° C.

The white precipitate formed was filtered, washed with water and dried under vacuum at room temperature. Obtained were 136 mg (0.29 mMol) of a white solid (yield 34%).

Analysis: $C_{20}H_{41}O_8PS$ (C,H).

EXAMPLE 4

4.1 DIETHYL DODECYLPHOSPHOTHIOLATE 6.25 ml (10 mMol) of nBuLi dissolved in hexane (1.6 M) were slowly added to a solution of 2.024 g (10 mMol) of 1-dodecylmercaptan in 10 ml of anhydrous THF, under stirring at 0° C. and under $N_2$ atmosphere.

The formation of a white precipitate was observed.

After 30 minutes at room temperature 1.44 ml (10 mMol) of diethyl chlorophosphate were slowly added.

After resolubilizing completely the precipitate, the solution was maintained under stirring for 1 h, then 5 ml of $H_2O$ were added and the mixture was extracted with diethyl ether. The ethereal extracts were dried on $Na_2SO_4$ and the solvent was evaporated under reduced pressure, thereby obtaining a colourless oil which was purified on a chromatographic column of silica gel (Merck n. 7734) by using as the eluent, a mixture of hexane/ethyl acetate 6:4. 3.04 g (9 mMol) of an oily product were obtained. The yield was 90%, Analysis: $C_{16}H_{35}O_3PS$ (C,H).

4.2 1-O-(DODECYLPHOSPHOTHIOLYL)-2,3,4,5,6-PENTA-O-BENZYL-MYO-INOSITOL 1 ml (7.3 mMol) of trimethylsilyl bromide were added to a solution of 822 mg (2.43 mMol) of diethyl dodecylphosphothiolate in 1 ml of anhydrous $CH_2Cl_2$ under stirring and under $N_2$ atmosphere.

The obtained solution was maintained for 6 h at room temperature, afterwards the solvent was evaporated under reduced pressure and a mixture consisting of 4 ml of anhydrous pyridine and 3 ml of anhydrous $CHCl_3$ was added.

2 ml (14.4 mMol) of triethylamine, 1.4 g (2.2 mMol) of D,L-2,3,4,5,6-penta-O-benzyl-myo-inositol and 2.94 g (9.72 mMol) of triisopropylbenzensulfonyl chloride (TiPSCl) were added to this mixture under stirring and under $N_2$ atmosphere.

After 48 h 10 ml of $H_2O$ were added and the solution was left For 30', after that it was acidified by means of a 0.5 M citric acid solution and extracted with $CHCl_3$. The organic extracts were washed at first with a citric acid solution, then with water, finally dried on $Na_2SO_4$ and the solvent was evaporated under reduced pressure. 3.50 g were obtained of a brown oil which was subsequently purified on a chromatographic column of silica gel (Merck n. 7734). The elution was carried out with the following gradient; chloroform, chloroform-methanol 96:4, chloroform-methanol 9:1.

Obtained were 1.33 g (1.48 mMol) of an oil with a yield of 61%.

Analysis: $C_{53}H_{67}O_8PS$ (C,H).

4.3 1-O-(DODECYLPHOSPHOTHIOLYL)-MYO-INOSITOL 5 ml of ethylmercaptan and 1.1 ml of boron trifluoride etherate were added under stirring and under $N_2$ atmosphere to a solution of 273 mg (0.3 mMol) of 1-O-(dodecylphosphothiolyl)-2,3,4,5,6-penta-O-benzyl-myo-inositol in 5 ml of anhydrous $CHCl_3$. The solution was maintained at room temperature fop 1 h, then 5 ml of $H_2O$ were added and the mixture was washed with ether, the aqueous phase was collected and evaporated under reduced pressure while maintaining the water temperature at 25° C.

The white precipitate formed was filtered, washed with water and dried under vacuum at room temperature. Obtained were 41 mg (0.092 mMol) of a white solid (yield 31%).

Analysis: $C_{18}H_{37}O_8PS$ (C,H).

EXAMPLE 5

5.1 DIETHYL OCTYLPHOSPHOTHIOLATE 6.25 ml (10 mMol) of nBuLi dissolved in hexane (1.6 M) were slowly added to a solution of 1.46 g (10 mMol) of 1-octylmercaptan in 10 ml of anhydrous THF under stirring at 0° C. and under $N_2$ atmosphere.

The formation of a white precipitate was observed.

After 30 minutes at room temperature 1.44 ml (10 mMol) of diethyl chlorophosphate were slowly added.

After resolubilizing completely the precipitate, the solution was maintained under stirring for 1 h, then 5 ml of $H_2O$ were added and the mixture was extracted with diethyl ether. The ethereal extracts were dried on $Na_2SO_4$ and the solvent was evaporated under reduced pressure, thereby obtaining a colourless oil which was purified on a chromatographic column of silica gel (Merck n. 7734) by using as the eluent a mixture of hexane/ethyl acetate 6:4. 2.54 g (9 mMol) of an oily product were obtained. The yield was 90%

Analysis: $C_{12}H_{27}O_3PS$ (C,H).

5.2 1-O-(OCTYLPHOSPHOTHIOLYL)-2,3,4,5,6-PENTA-O-BENZYL-MYO-INOSITOL 1 ml (7.3 mMol) of trimethylsilyl bromide were added to a solution of 0.685 g (2.43 mMol) of diethyl octylphosphothiolate in 1 ml of anhydrous $CH_2Cl_2$ under stirring and under $N_2$ atmosphere.

The obtained solution was maintained for 6 h at room temperature, afterwards the solvent was evaporated under reduced pressure and a mixture consisting of 4 ml of anhydrous pyridine and 3 ml of anhydrous $CHCl_3$ was added.

2 ml (14.4 mMol) of triethylamine, 1.4 g (2.2 mMol) of D,L-2,3,4,5,6-penta-O-benzyl-myo-inositol and 2.94 g (9.72 mMol) of triisopropylbenzensulfonyl chloride (TiPSCl) were added to this mixture under stirring and under $N_2$ atmosphere.

After 48 h 10 ml of $H_2O$ were added and the solution was left 30', after that it was acidified by means of a 0.5 M citric acid solution and extracted with $CHCl_3$. The organic extracts were washed at first with a citric acid solution, then with water, finally dried on $Na_2SO_4$ and the solvent was evaporated under reduced pressure. 2.70 g were obtained of a brown oil which was subsequently purified on a chromatographic column of silica gel (Merck n. 7734). The elution was carried out with the following gradient; chloroform, chloroform-methanol 96:4, chloroform-methanol 9:1.

Obtained were 1.120 g (1.31 mMol) of an oil with a yield of 54%.

Analysis: $C_{49}H_{59}O_8PS$ (C,H).

5.3 1-O-(OCTYLPHOSPHOTHIOLYL)-MYO-INOSITOL 5 ml of ethylmercaptan and 1.1 ml of boron trifluoride etherate were added under stirring and under $N_2$ atmosphere to a solution of 201 mg (0.24 mMol) of 1-O-(octylphosphothiolyl)-2,3,4,5,6-penta-O-benzyl-myo-inositol in 5 ml of anhydrous $CHCl_3$. The solution was maintained at room temperature for 1 h, then 5 ml of $H_2O$ were added and the mixture was washed with ether, the aqueous phase was collected and evaporated under reduced pressure while maintaining the water temperature at 25° C.

The white precipitate formed was filtered, washed with water and dried under vacuum at room temperature. Obtained were 28 mg (0.072 mMol) of a white solid (yield 30%)

Analysis: $C_{14}H_{29}O_8PS$ (C,H).

EXAMPLE 6

6.1 rac-1,1'-DITHIOBIS(2,3-O-ISOPROPYLIDEN-PROPANE)

1.046 g (4.88 mMol) of rac-1,1'-dithiobis(2,3-propylene glycol), prepared according to J. W. Cox, and other, Chem. Phys. Lipids, 25, 369–380, (1979), were dissolved in 10 ml of DMF. 8 ml of 2,2-dimethoxypropane and 20 mg of para-toluenesulfonic acid were added to this solution. The solution was maintained under stirring for 1 h at room temperature, then 20 ml of water were added and the mixture was extracted with $CH_2Cl_2$; the organic extracts were washed three times with 100 ml of $H_2O$ and dried on $Na_2SO_4$.

The solvent was evaporated under vacuum and 1.056 g were obtained of a yellow oil that could be used without further purifications. 6.2 rac-1-MERCAPTO-2,3-O-ISOPROPYLIDENPROPANE 1.050 g (6.8 mMol) of dithioerythrol were added to 1 g (3.4 mMol of rac-1,1'-dithiobis(2,3-O-isopropylidenpropane) dissolved in 75 ml of ethanol.

33% $NH_4OH$ was added until a pH value of 9.6 was reached. After 90' the solution was concentrated under vacuum while maintaining a temperature of 30° C., until its volume was reduced to 20 ml. 100 ml of a mixture diethyl ether/hexane 1:1 were added and the obtained solution was washed with water until dithiothreitol was completely removed. The organic extracts were dried on $Na_2SO_4$, and the solvent was evaporated under vacuum. Obtained were 530 mg of a yellow oil that could be used without further purifications. An analytical sample was obtained by using silica gel chromatography and as the eluent $CH_2Cl_2$.

Analysis: $C_6H_{12}O_2S$ (C,H).

$^1$H-NMR (80 MHz, $CDCl_3$): δ 1.36 (m,6H), 1.51 (m,1H), 2.62(m,2H), 3.62–4.25(m,3H).

6.3 ETHYL 2,3-O-ISOPROPYLIDENPROPYL-1-PHOSPHOTHIOLATE.

2.5 ml of n-BuLi dissolved in such an amount of hexane that a concentration 1.6 M was obtained, were added to a solution of 533 mg (3.6 mMol) of rac-1-mercapto-2,3-O-isopropylidenpropane in 10 ml of anhydrous THF while maintaining a temperature between 0 and 5° C. After 15 min at room temperature 0.6 ml of diethylchlorophosphate (4 mMol) were added. After 30 min 10 ml of water were added and the mixture was extracted with $CH_2Cl_2$. The organic extracts were washed three times with 20 ml of $H_2O$ and dried on $Na_2SO_4$. The solvent was evaporated under vacuum obtaining 821 mg of a yellow oil that could be used without further purifications.

An analytical sample was obtained by using silica gel chromatography and as the eluent a mixture of diethyl ether/hexane 4:1.

Analysis: $C_{10}H_{21}O_5PS$ (C,H).

6.4 ETHYL 2,3-DI-O-STEAROYLPROPYL-1-PHOSPHOTHIOLATE.

400 mg of anhydrous $ZnCl_2$ and 2 ml (6 mMol) of stearoyl chloride were added to a solution of 853 mg (3 mMol) of ethyl 2,3-O-isopropylidenpropyl-1-phosphothiolate in 3 ml of anhydrous ether. The solution was left at room temperature for 3 h, then 10 ml of water were added and finally it was extracted with ether. The organic extracts were washed three times with 20 ml of $H_2O$ and dried on $Na_2SO_4$.

The solvent was evaporated under vacuum and 2.201 mg of a yellow solid was obtained. Finally the solid was purified using silica gel chromatography by eluting with diethyl ether/hexane 1:1.

Obtained were 1.396 g (1.8 mMol) of a pale yellow solid with a yield of 37.5% calculated on the rac-1,1'-dithiobis (2,3-propylene glycol).

Analysis: $C_{47}H_{85}O_7PS$ (C,H).

$^1$H-NMR (80 MHz, $CDCl_3$): δ0.85(m,6H), 1.33(m,66H), 2.30(t,J6,7Hz,4H), 3.10(m,2H), 4.25 (m,6H), 5.25(m,1H).

6.5 1-O-(2,3-DISTEAROYLOXYPROPYLPHOSPHOTHIOLYL)-2,3,4,5,6-PENTA-O-BENZYL-MYO-INOSITOL.

0.66 ml (5.04 mMol) of trimethylsilylbromide were added to a solution of 978 mg (1.26 mMol) of 2,3-di-O-stearoylpropyl-1-ethyl phosphothiolate in 0.5 ml of anhydrous $CH_2Cl_2$.

The obtained solution was maintained for 5 h at room temperature, then the solvent was evaporated under reduced pressure and 4 ml of anhydrous pyridine were added. 1 ml (7.2 mMol) of triethylamine, 700 mg (1.1 mMol) of D,L 2,3,4,5,6-penta-O-benzyl-myo-inositol and 1.450 g (4.79 mMol) of triisopropylbenzensulfonylchloride (TiPSCl) were added to this solution under stirring and under $N_2$ atmosphere.

After 48 h 10 ml of $H_2O$ were added and the mixture was left for 30' after that it was acidified with a 0.5 M solution of citric acid and extracted with $CHCl_3$.

The organic extracts were washed with a citric acid solution, then with water, finally dried on $Na_2SO_4$ and the solvent was evaporated under reduced pressure.

Obtained were 2.5 g of a brown oil which was purified by using a chromatographic column of silica gel (Merck n. 7734).

The elution was carried out with the following gradient: chloroform, chloroform-methanol 96:4, chloroform-methanol 85:15. 721 mg (0.54 mMol) of an oil were obtained with a yield of 43%.

Analysis: $C_{80}H_{117}O_{12}PS$ (C,H).

6.6 1-O-(2,3-DISTEAROYLOXYPROPYLPHOSPHOTHIOLYL)-MYO-INOSITOL 5 ml of ethylmercaptan and 1.1 ml of boron trifluoride etherate were added to a solution of 320 mg (0.24 mMol) of 1-O-(2,3-diasteroyloxypropylphosphothiolyl)-2,3,4,5,6-penta-O-benzyl-myo-inositol in 5 ml of anhydrous $CHCl_3$ under stirring and under $N_2$ atmosphere. The solution was maintained at room temperature for 1 h, then 5 ml of $H_2O$ were added and the mixture was washed with ether, the aqueous phase was collected and evaporated under reduced pressure while maintaining the water temperature at 25° C.

The white precipitate formed was filtered, washed with water and dried under vacuum at room temperature. Obtained were 34 mg (0.038 mMol) of a white solid (yield 16%).

Analysis: $C_{45}H_{87}O_{12}PS$ (C,H).

EXAMPLE 7

7.1 ETHYL 2,3-DI-O-PALMITOYLPROPYL-1-PHOSPHOTHIOLATE.

400 mg of anhydrous $ZnCl_2$ and 1.8 ml (6 mMol) of palmitoyl chloride were added to a solution of 853 mg (3 mMol) of ethyl 2,3-O-isopropylidenpropyl-1-phosphothiolate in 3 ml of anhydrous ether. The solution was left at room temperature for 3 h, then 10 ml of water were added and finally it was extracted with ether. The organic extracts were washed three times with 20 ml of $H_2O$ and dried on $Na_2SO_4$.

The solvent was evaporated under vacuum and 2.071 g of a yellow solid were obtained. Finally the solid was purified by silica gel chromatography using as the eluent diethyl ether/hexane 1:1.

Obtained were 1.225 g (1.7 mMol) of a pale yellow solid with a yield of 35%, calculated on rac-1,1'-dithiobis (2,3-propylene glycol).

Analysis: $C_{39}H_{77}O_7PS$ (C,H).

$^1$H-NMR (80 MHz, CDCl$_3$): δ0.85(m,6H), 1.33(m,62H), 2.30(t,J6,7Hz,4H), 3.10(m,2H), 4.25(m,6H), 5.25(m,1H). 7.2 1-O-(2,3-DIPALMITOYLOXYPROPYLPHOSPHOTHIOLYL)-2,3,4,5,6-PENTA-O-BENZYL-MYO-INOSITOL.

0.66 ml (5.04 mMol) of trimethylsilylbromide were added to a solution of 908 mg (1.26 mMol) of ethyl 2,3-di-O-palmitoylpropyl1-phosphothiolate in 0.5 ml of anhydrous CH$_2$Cl$_2$.

The mixture was maintained for 5 h at room temperature under stirring, then the solvent was evaporated under reduced pressure and 4 ml of anhydrous pyridine were added. 1 ml (7.2 mMol) of triethylamine, 700 mg (1.1 mMol) of D,L 2,3,4,5,6-penta-O-benzyl-myo-inositol and 1.450 g (4.79 mMol) of triisopropylbenzensulfonylchlofide (TiPSCl) were added to this solution under stirring and under N$_2$ atmosphere.

After 48 h 10 ml of H$_2$O were added and the mixture was left for 30' after that it was acidified with a solution 0.5 M of citric acid and extracted with CHCl$_3$.

The organic extracts were washed with a citric acid solution, then with water, finally dried on Na$_2$SO$_4$ and the solvent was evaporated under reduced pressure.

Obtained were 3.9 g of a brown oil which was purified by using a chromatographic column of silica gel (Merck n. 7734).

The elution was carried out with the following gradient: chloroform, chloroform-methanol 96:4, chloroform-methanol 85:15. 626 mg (0.49 mMol) of an oil were obtained with a yield of 39%

Analysis: $C_{76}H_{109}O_{12}PS$ (C,H).

7.3 1-O-(2,3-DIPALMITOYLOXYPROPYLPHOSPHOTHIOLYL)-MYO-INOSITOL 5 ml of ethylmercaptan and 1.1 ml of boron trifluoride etherate were added to a solution of 306 mg (0.24 mMol) of 1-O-(2,3-dipalmitoyloxypropylphosphothiolyl)-2,3,4,5,6-penta-O-benzyl-myo-inositol in 5 ml of anhydrous CHCl$_3$ under stirring and under N$_2$ atmosphere. The solution was maintained at room temperature for 1 h, then 5 ml of H$_2$O were added and the mixture was washed with ether, the aqueous phase was collected and evaporated under reduced pressure while maintaining the water temperature at 25° C.

The white precipitate formed was filtered, washed with water and dried under vacuum at room temperature. Obtained were 35 mg (0.043 mMol) of a white solid (yield 18%).

Analysis: $C_{41}H_{79}O_{12}PS$ (C,H).

EXAMPLE 8

8.1 ETHYL 2,3-DI-O-MYRISTOYLPROPYL-1-PHOSPHOTHIOLATE.

400 mg of anhydrous ZnCl$_2$ and 1.3 ml (6 mMol) of myristoyl chloride were added to a solution of 853 mg (3 mMol) of ethyl 2,3-O-isopropylidenpropyl-l-phosphothiolate in 3 ml of anhydrous ether. The solution was left at room temperature for 3 h, then 10 ml of water were added and finally it was extracted with ether. The organic extracts were washed three times with 20 ml of H$_2$O and dried on Na$_2$SO$_4$.

The solvent was evaporated under vacuum and 1.954 g were obtained of a yellow solid which was purified using silica gel chromatography, eluting with diethyl ether/hexane 1:1.

Obtained were 1.6 g (2.4 mMol) of a pale yellow solid with a yield of 50%, calculated on rac-1,1'-dithiobis (2,3-propylene glycol).

Analysis: $C_{35}H_{69}O_7PS$ (C,H).

8.2 1-O-(2,3-DIMYRISTOYLOXYPROPYLPHOSPHOTHIOLYL)-2,3,4,5,6-PENTA-O-BENZYL-MYO-INOSITOL.

0.66 ml (5.04 mMol) of trimethylsilylbromide were added to a solution of 838 mg (1.26 mMol) of ethyl 2,3-di-O-dimiristoylpropyl-1-phosphothiolate in 0.5 ml of anhydrous CH$_2$Cl$_2$.

The mixture obtained was maintained for 5 h under stirring at room temperature, then the solvent was evaporated under reduced pressure and 4 ml of anhydrous pyridine were added. 1 ml (7.2 mMol) of triethylamine, 700 mg (1.1 mMol) of D,L 2,3,4,5,6-penta-O-benzyl-myo-inositol and 1.450 g (4.79 mMol) of triisopropyl-benzensulfonylchloride (TiPSCl) were added to this solution under stirring and under N$_2$ atmosphere.

After 48 h 10 ml of H$_2$O were added and the mixture was left for 30' after that it was acidified with a solution 0.5 M of citric acid and extracted with CHCl$_3$.

The organic extracts were washed with a citric acid solution, then with water, finally dried on Na$_2$SO$_4$ and the solvent was evaporated under reduced pressure.

Obtained were 2.5 g of a brown oil which was purified by using a chromatographic column of silica gel (Merck n. 7734).

The elution was carried out with the following gradient: chloroform, chloroform-methanol 96:4, chloroform-methanol 85:15. 585 mg (O-479 mMol) of an oil were obtained with a yield of 38%.

Analysis: $C_{72}H_{101}O_{12}PS$ (C,H).

8.3 1-O-(2,3-DIMYRISTOYLOXYPROPYLPHOSPHOTHIOLYL)-MYO-INOSITOL 5 ml of ethylmercaptan and 1.1 ml of boron trifluoride etherate were added to a solution of 293 mg (0.24 mMol) of 1-O-(2,3-dimyristoyloxypropylphosphothiolyl)-2,3,4,5,6-penta-O-benzyl-myoinositol in 5 ml of anhydrous CHCl$_3$ under stirring and under N$_2$ atmosphere. The mixture was maintained at room temperature for 1 h, then 5 ml of H$_2$O were added and the mixture was washed with ether, the aqueous phase was collected and evaporated under reduced pressure while maintaining the water temperature at 25° C.

The white precipitate formed was filtered, washed with water and dried under vacuum at room temperature. Obtained were 46 mg (0.06 mMol) of a white solid (yield 25%).

Analysis: $C_{37}H_{71}O_{12}PS$ (C,H).

EXAMPLE 9

9.1 ETHYL 2,3-DI-O-LAUROYLPROPYL-1-PHOSPHOTHIOLATE.

400 mg of anhydrous ZnCl$_2$ and 1.2 ml (6 mMol) of lauroyl chloride were added to a solution of 853 mg (3 mMol) of ethyl 2,3-O-isopropylidenpropyl-1-phosphothiolate in 3 ml of anhydrous ether. The mixture was left at room temperature for 3 h, then 10 ml of water were added and finally it was extracted with ether. The organic extracts were washed three times with 20 ml of H$_2$O and dried on Na$_2$SO$_4$.

The solvent was evaporated under vacuum and 2.005 g of a yellow solid were obtained. Finally the solid was purified by silica gel chromatography, eluting with diethyl ether/hexane 1:1.

Obtained were 1.096 g (1.8 mMol) of a pale yellow solid with a yield of 37%, calculated on the rac-1,1'-dithiobis (2,3-propylen glycol).

Analysis: $C_{31}H_{61}O_7PS$ (C,H).

9.2 1-O-(2,3-DILAUROYLOXYPROPYLPHOSPHOTHIOLYL)-2,3,4,5,6-PENTA-O-BENZYL-MYO-INOSITOL.

0.66 ml (5.04 mMol) of trimethylsilylbromide were added to a solution of 767 mg (1.26 mMol) of ethyl 2,3-di-O-lauroylpropyl-1-phosphothiolate in 0.5 ml of anhydrous $CH_2Cl_2$.

The mixture obtained was maintained under stirring for 5 h at room temperature, then the solvent was evaporated under reduced pressure and 4 ml of anhydrous pyridine were added. 2 ml (14.4 mMol) of triethylamine, 1.4 g (2.2 mMol) of D,L 2,3,4,5,6-penta-O-benzyl-myo-inositol and 2.94 g (9-72 mMol) of triisopropylbenzensulfonylchloride (TiPSCl) were added to this solution under stirring and under $N_2$ atmosphere.

After 48 h 10 ml of $H_2O$ were added and the mixture was left for 30' after that it was acidified with a solution 0.5 M of citric acid and extracted with $CHCl_3$.

The organic extracts were washed with a citric acid solution, then with water, finally dried on $Na_2SO_4$ and the solvent was evaporated under reduced pressure.

Obtained were 2.05 g of a brown oil which was purified by using a chromatographic column of silica gel (Merck n. 7734).

The elution was carried out with the following gradient: chloroform, chloroform-methanol 96:4, chloroform-methanol 85:15. 910 mg (0.78 mMol) of an oil were obtained with a yield of 62%.

Analysis: $C_{68}H_{93}O_{12}PS$ (C,H).

9.3 1-O-(2,3-DILAUROYLOXYPROPYLPHOSPHOTHIOLYL)-MYO-INOSITOL 5 ml of ethylmercaptan and 1.1 ml of boron trifluoride etherate were added to a solution of 280 mg (0.24 mMol) of 1-O-(2,3-dilauroyloxypropylphosphothiolyl)-2,3,4,5,6-penta-O-benzyl-myo-inositol in 5 ml of anhydrous $CHCl_3$ under stirring and under $N_2$ atmosphere. The mixture was maintained at room temperature for 1 h, then 5 ml of $H_2O$ were added and the mixture was washed with ether, the aqueous phase was collected and evaporated under reduced pressure while maintaining the water temperature at 25° C.

The white precipitate was filtered, washed with water and dried under vacuum at room temperature. Obtained were 35 mg (0.048 mMol) of a white solid (yield 20%).

Analysis: $C_{33}H_{63}O_{12}PS$ (C,H).

EXAMPLE 10

10.1 ETHYL 2,3-DI-O-OCTANOYLPROPYL-1-PHOSPHOTHIOLATE.

400 mg of anhydrous $ZnCl_2$ and 1 ml (6 mMol) of octanoyl chloride were added to a solution of 853 mg (3 mMol) of ethyl 2,3-O-isopropylidenpropyl-1-phosphothiolate in 3 ml of anhydrous ether. The mixture was left at room temperature for 3 h, then 10 ml of water were added and finally it was extracted with ether. The organic extracts were washed three times with 20 ml of $H_2O$ and dried on $Na_2SO_4$.

The solvent was evaporated under vacuum and 1.154 g of a Fellow solid were obtained. Finally the solid was purified by silica gel chromatography, eluting with diethyl ether/hexane 1:1.

Obtained were 994 mg (2 mMol) of a pale yellow solid with a yield of 41%, calculated on the rac-1,1'-dithiobis (2,3-propylene glycol).

Analysis: $C_{23}H_{45}O_7PS$ (C,H). 10.2 1-O-(2,3-DIOCTANOYLOXYPROPYLPHOSPHOTHIOLYL)-2,3,4,5,6-PENTA-O-BENZYL-MYO-INOSITOL.

0.66 ml (5.04 mMol) of trimethylsilylbromide were added to a solution of 626 mg (1.26 mMol) of ethyl-2,3-di-O-octanoylpropyl-1-phosphothiolate in 0.5 ml of anhydrous $CH_2Cl_2$.

The mixture obtained was maintained under stirring for 5 h at room temperature, then the solvent was evaporated under reduced pressure and 4 ml of anhydrous pyridine were added. 1 ml (7.2 mMol) of triethylamine, 700 mg (1.1 mMol) of D,L 2,3,4,5,6-penta-O-benzyl-myo-inositol and 1.45 g (4.79 mMol) of triisopropylbenzensulfonylchloride (TiPSCl) were added to this solution under stirring and under $N_2$ atmosphere.

After 48 h 10 ml of $H_2O$ were added and the mixture was left for 30'after that it was acidified with a solution 0.5 M of citric acid and extracted with $CHCl_3$.

The organic extracts were washed with a citric acid solution, then with water and finally dried on $Na_2SO_4$ and the solvent was evaporated under reduced pressure.

Obtained were 1.605 g of a brown oil which was purified by using a silica gel chromatographic column (Merck n. 7734)

The elution was carried out with the following gradient: chloroform, chloroform-methanol 96:4, chloroform-methanol 85:15. 832 mg (0.79 mMol) of an oil were obtained with a yield of 63%.

Analysis: $C_{60}H_{77}O_{12}PS$ (C,H).

10.3 1-O-(2,3-DIOCTANOYLOXYPROPYLPHOSPHOTHIOLYL)-MYO-INOSITOL 5 ml of ethylmercaptan and 1.1 ml of boron trifluoride etherate were added to a solution of 253 mg (0.24 mMol) of 1-O-(2,3-dioctanoyloxypropylphosphothiolyl)-2,3,4,5,6-penta-O-benzyl-myoinositol in 5 ml of anhydrous $CHCl_3$ under stirring and under $N_2$ atmosphere. The mixture was maintained at room temperature for 1 h, then 5 ml of $H_2O$ were added and said mixture was washed with ether, the aqueous phase was collected and evaporated under reduced pressure while maintaining the water temperature at 25° C.

The white precipitate formed was filtered, washed with water and dried under vacuum at room temperature. Obtained were 33 mg (0.055 mMol) of a white solid (yield 23%).

Analysis: $C_{25}H_{47}O_{12}PS$ (C,H).

EXAMPLE 11

11.1 1-BENZYLTHIO-2,3-PROPYLENE GLYCOL.

1 ml of 1-thioglycerol (11.5 mMol) was added to 6 ml of a mixture of 2N sodium hydroxide / ethanol 1:1.

Subsequently 1.33 ml of benzyl chloride (11.5 mMol) were added drop by drop to this solution maintained under stirring. After 15 minutes 15 ml of $CH_2Cl_2$ were added, then the mixture was washed with water until a neutral pH was reached. The organic phase was dried on anhydrous sodium sulfate and the solvent was evaporated under reduced pressure; obtained were 1.622 g of a clear oil. The yield was 72%.

Analysis: $C_{10}H_{14}O_2S$ (C,H).

11.2 1-BENZYLTHIO-2,3-DIOCTADECYLOXYPROPYLEN GLYCOL.

A suspension consisting of 1.770 g of potassium hydroxide and 1.110 g (5.61 mMol) of 1-benzylthio-2,3- propylen glycol dissolved in 60 ml of xylene was brought to boiling temperature under vigorous stirring. After 1 h a solution of 2.412 g (6.9 mMol) of octadecylmethansulfonate in 15 ml of xylene was added. The mixture was left under reflux for 4 h, then it was diluted with diethyl ether. The mixture was washed with water until washing water neutrality was reached. The organic extracts were dried on $Na_2SO_4$ and the solvent was evaporated under reduced pressure. Obtained were 2.150 g of a very thick pale yellow oil which was purified by silica gel chromatography using as the eluent a mixture of hexane / diethyl ether 95:5. Obtained were 1.440 g of product. The yield was 36.5%.

Analysis: $C_{46}H_{86}O_2S$ (C,H).

11.3 2,3-DIOCTADECYLOXY-1-MERCAPTO-2,3-PROPYLEN GLYCOL

A solution consisting of 75 ml of butanol and 1.055 g (1.5 mMol) of 1-benzylthio-2,3-dioctadecyloxy-2,3-propylen glycol was brought to reflux temperature, then 1.8 g of sodium were added; the mixture was left under reflux until sodium complete dissolution. Afterwards the solution was cooled to room temperature and diluted with 80 ml of $CHCl_3$; the organic phase was washed with a 1N citric acid solution until reaching an acid pH then with water until reaching washing water neutrality. The organic extracts were dried on $Na_2SO_4$ and the solvent was evaporated under reduced pressure. Obtained were 413 mg (0.675 mMol) of an oil with a yield of 45%.

Analysis: $C_{39}H_{80}O_2S$ (C,H).

11.4 ETHYL 2,3-DIOCTADECYLOXYPROPYL-PHOSPHOTHIOLATE.

4.4 ml of n-BuLi (1.6 M) in hexane were added to a solution of 4.292 g (7 mMol) of 2,3-dioctadecyloxy-1-mercapto-2,3-propylen glycol in 10 ml of anhydrous THF under $N_2$ atmosphere; the mixture was stirred for 30' and during this time the formation of a white precipitate was observed. 1.2 g (7 mMol) of diethylchlorophosphate were added; after 1 h 5 ml of water were added and the mixture was extracted with diethyl ether. The ethereal extracts were dried on $Na_2SO_4$ and the solvent was evaporated under reduced pressure thereby obtaining a colourless oil which was purified on a silica gel chromatographic column using as the eluent a mixture of hexane/ethyl acetate Obtained were 3.147 g (4.2 mMol) of an oil with a yield of 60

Analysis: $C_{43}H_{89}O_5PS$ (C,H).

11.5 1-O-(2,3-DIOCTADECYLOXYPROPYL-PHOSPHOTHIOLYL)-2,3,4,5,6-PENTA-O-BENZYL-MYO-INOSITOL 1 ml (7.3 mMol) of trimethylsilyl bromide was added to a solution of 1.820 g (2.43 mMol) of ethyl 2,3-dioctadecyloxypropylphosphothiolate in 1 ml of anhydrous $CH_2Cl_2$ under stirring and under $N_2$ atmosphere.

The mixture obtained was maintained for 6 h at room temperature, afterwards the solvent was evaporated under reduced pressure and a mixture consisting of 4 ml of anhydrous pyridine and 3 ml of anhydrous $CHCl_3$ was added.

2 ml (14.4 mMol) of triethylamine, 1.4 g (2.2 mMol) of D,L-2,3,4,5,6-penta-O-benzyl-myo-inositol and 2.94 g (9.72 mMol) of triisopropylbenzensulfonyl chloride (TiPSCl) were added to this mixture under stirring and under $N_2$ atmosphere.

After 48 h 10 ml of $H_2O$ were added and the solution was left for 30', after that it was acidified by means of a 0.5 M citric acid solution and extracted with $CHCl_3$. The organic extracts were washed at first with a citric acid solution, then with water finally dried on $Na_2SO_4$ and the solvent was evaporated under reduced pressure. 4.3 g were obtained of a brown oil which was subsequently purified on a chromatographic column of silica gel (Merck n. 7734). The elution was carried out with the following gradient; chloroform, chloroform-methanol 96:4, chloroform-methanol 85:15.

Obtained were 2.063 g (1.58 mMol) of an oil with a yield of 65%.

Analysis: $C_{80}H_{121}O_{10}PS$ (C,H).

11.6 1-O-(2,3-DIOCTADECYLOXYPROPYL-PHOSPHOTHIOLYL)-MYO-INOSITOL.

5 ml of ethylmercaptan and 1.1 ml of boron trifluoride etherate were added to a solution of 313 mg (0.24 mMol) of 1-O-(2,3-dioctadecyloxypropyl-phosphothiolyl)- 2,3,4,5,6-penta-O-benzyl-myo-inositol in 5 ml of anhydrous $CHCl_3$ under stirring and under $N_2$ atmosphere. The mixture was maintained at room temperature for 1 h, then 5 ml of $H_2O$ were added and said mixture was washed with ether, the aqueous phase was collected and evaporated under reduced pressure while maintaining the water temperature at 25° C.

The white precipitate formed was filtered, washed with water and dried under vacuum at room temperature. Obtained were 47 mg (0.055 mMol) of a white solid (yield 23%).

Analysis: $C_{45}H_{91}O_{10}PS$ (C,H).

EXAMPLE 12

12.1 1-BENZYLTHIO-2,3-DIHEXADECYLOXY-PROPYLEN GLYCOL.

A suspension consisting of 1.770 g of potassium hydroxide and 1.110 g (5.61 mMol) of 1-benzylthio-2,3-propylen glycol dissolved in 60 ml of xylene was brought to reflux under vigorous stirring. After 1 h a solution of 2.211 g (6.9 mMol) of hexadecylmethansulfonate in 15 ml of xylene were added. The mixture was left under reflux for 4 h, then it was diluted with diethyl ether. The mixture was washed with water until reaching washing water neutrality. The organic extracts were dried on $Na_2SO_4$ and the solvent was evaporated under reduced pressure. Obtained were 1.950 g of a very thick pale yellow oil which was purified by silica gel chromatography using as the eluent a mixture of hexane / diethyl ether 95:5. Obtained were 1,230 g of product. The yield was 34%.

Analysis: $C_{42}H_{78}O_2S$ (C,H).

12.2 2,3-DIHEXADECYLOXY-1-MERCAPTO-2,3-PROPYLEN GLYCOL

A solution consisting of 75 ml of butanol and 971 mg (1.5 mMol) of 1-benzylthio-2,3-dihexadecyloxy-2,3-propylen glycol was brought to reflux temperature, then 1.478 g of sodium were added; the mixture was left under reflux until sodium complete dissolution. Afterwards the solution was cooled to room temperature and diluted with 80 ml of $CHCl_3$; the organic phase was washed with 1 N citric acid solution until reaching an acid pH, then with water until reaching neutrality. The organic extracts were dried on $Na_2SO_4$ and the solvent was evaporated under reduced pressure.

Obtained were 459 mg (0.825 mMol) of an oil with a yield of 55

Analysis: $C_{35}H_{72}O_2S$ (C,H).

12.3 ETHYL 2,3-DIHEXADECYLOXYPROPYL-PHOSPHOTHIOLATE.

4.4 ml of n-BuLi (1.6 M) in hexane were added to a solution of 3.9 g (7 mMol) of 2,3-hexadecyloxy-1-mercapto-2,3-propylen glycol in 10 ml of anhydrous THF under $N_2$ atmosphere; the solution was stirred for 30' and during this time the formation of a precipitate was observed. 1.2 g (7 mMol) of diethylchlorophosphate were added; after 1 h, 5 ml of water were added and the solution was extracted with diethyl ether. The ethereal extracts were dried on $Na_2SO_4$ and the solvent was evaporated under reduced pressure, thereby obtaining a colourless oil which was purified on a silica gel chromatographic column using as the eluent a mixture of hexane / ethyl acetate Obtained were 3.01 g (4.34 mMol) of an oil with a yield of 62%.

Analysis: $C_{39}H_{81}O_5PS$ (C,H).

12.4 1-O-(2,3-DIHEXADECYLOXYPROPYL-PHOSPHOTHIOLYL)-2,3,4,5,6-PENTA-O-BENZYL-MYO-INOSITOL 1 ml (7.3 mMol) of trimethylsilyl bromide was added to a solution of 1.684 g (2.43 mMol) of ethyl-2,3-dihexadecyloxypropylphosphothiolate in 1 ml of anhydrous $CH_2Cl_2$ under stirring and under $N_2$ atmosphere.

The mixture was maintained for 6 h at room temperature, afterwards the solvent was evaporated under reduced pressure and a mixture consisting of 4 ml of anhydrous pyridine and 3 ml of anhydrous $CHCl_3$ was added.

2 ml (14.4 mMol) of triethylamine, 1.4 g (2.2 mMol) of D,L-2,3,4,5,6-penta-O-benzyl-myo-inositol and 2.9 g (9.72 mMol) of triisopropylbenzensulfonyl chloride (TiPSCl) were added to this mixture under stirring and under $N_2$ atmosphere.

After 48 h 10 ml of $H_2O$ were added and the solution was left for 30', after that it was acidified by means of a 0.5 M citric acid solution and extracted with $CHCl_3$. The organic extracts were washed at first with a citric acid solution, then with water, finally dried on $Na_2SO_4$ and the solvent was evaporated under reduced pressure. 4.15 g were obtained of a brown oil which was subsequently purified on a chromatographic column of silica gel (Merck n. 7734). The elution was carried out with the following gradient; chloroform, chloroform-methanol 96:4, chloroform-methanol 85:15.

Obtained were 2.062 g (1.65 mMol) of an oil with a yield of 68%.

Analysis: $C_{76}H_{113}O_{10}PS$ (C,H).

12.5 1-O-(2,3-DIHEXADECYLOXYPROPYL-PHOSPHOTHIOLyL)-MYO-INOSITOL.

5 ml of ethylmercaptan and 1.1 ml of boron trifluoride etherate were added to a solution of 300 mg (0.24 mMol) of 1-O-(2,3-dihexadecyloxypropyl-phosphothiolyl)-2,3,4,5,6-penta-O-benzyl-myo-inositol in 5 ml of anhydrous $CHCl_3$ under stirring and under $N_2$ atmosphere. The mixture was maintained at room temperature for 1 h, then 5 ml of $H_2O$ were added, and said mixture was washed with ether, the aqueous phase was collected and evaporated under reduced pressure while maintaining the water temperature at 25° C.

The white precipitate formed was filtered, washed with water and dried under vacuum at room temperature. Obtained were 48 mg (0.06 mMol) of a white solid (yield 25° C.

Analysis: $C_{41}H_{83}O_{10}PS$ (C,H).

EXAMPLE 13

13.1 1-BENZYLTHIO-2,3-DITETRADECYLOXY-2,3-PROPYLEN GLYCOL.

A suspension consisting of 1.770 g of potassium hydroxide and 1.110 g (5.61 mMol) of 1-benzylthio-2,3-propylen glycol in 60 ml of xylene was brought to reflux under vigorous stirring. After 1 h a solution of 2.016 g (6.9 mMol) of tetradecylmethansulfonate in 15 ml of xylene was added. The mixture was left under reflux for 4 h, then it was diluted with diethyl ether. The solution was washed with water until reaching washing water neutrality. The organic extracts were dried on $Na_2SO_4$ and the solvent was evaporated under reduced pressure. Obtained were 1.825 g of a very thick yellow oil which was purified by silica gel chromatography using as the eluent a mixture of hexane / diethyl ether 95:5. Obtained were 1,200 g of product. The yield was 36%.

Analysis: $C_{38}H_{70}O_2S$ (C,H).

13.2 2,3-DITETRADECYLOXY-1-MERCAPTO-2,3-PROPYLEN GLYCOL

A solution consisting of 75 ml of butanol and 886 mg (1.5 mMol) of 1-benzylthio-2,3-ditetradecyloxy-2,3-propylen-glycol was brought to reflux, then 1.344 g of sodium were added; the mixture was left under reflux until sodium complete dissolution.

Afterwards the solution was cooled to room temperature and diluted with 80 ml of $CHCl_3$; the organic phase was washed with a 1 N citric acid solution until reaching an acid pH then with water until reaching neutrality. The organic extracts were dried on $Na_2SO_4$ and the solvent was evaporated under reduced pressure. Obtained were 398 mg (0.795 mMol) of an oil with a yield of 53%

Analysis: $C_{31}H_{64}O_2S$ (C,H).

13.3 ETHYL 2,3-DITETRADECYLOXY-PROPYLPHOSPHOTHIOLATE.

4.4 ml of n-BuLi (1.6 M) in hexane were added to a solution of 3.5 g (7 mMol) of 2,3-ditetradecyloxy-1-mercapto-2,3-propylen glycol in 10 ml of anhydrous THF under $N_2$ atmosphere; the solution was stirred for 30' and during this time the formation of a white precipitate was observed. 1.2 g (7 mMol) of diethylchlorophosphate were added; after 1 h, 5 ml of water were added and the solution was extracted with diethyl ether. The ethereal extracts were dried on $Na_2SO_4$ and evaporated under reduced pressure thereby obtaining a colourless oil which was purified on a silica gel chromatographic column using as the eluent a mixture of hexane / ethyl acetate 6:4. Obtained were 2.898 g (4-55 mMol) of an oil with a yield of 65%.

Analysis: $C_{35}H_{73}O_5PS$ (C,H).

13.4 1-O-(2,3-DITETRADECYLOXYPROPYL-PHOSPHOTHIOLYL)-2,3,4,5,6-PENTA-O-BENZYL-MYO-INOSITOL 1 ml (7.3 mMol) of trimethylsilyl bromide was added to a solution of 1.548 g (2.43 mMol) of ethyl-2,3-ditetradecyloxypropylphosphothiolate in 1 ml of anhydrous $CH_2Cl_2$ under stirring and under $N_2$ atmosphere.

The mixture was maintained for 6 h at room temperature, afterwards the solvent was evaporated under reduced pressure and a mixture composed by 4 ml of anhydrous pyridine and 3 ml of anhydrous $CHCl_3$ was added.

2 ml (14.4 mMol) of triethylamine, 1.4 g (2.2 mMol) of D,L-2,3,4,5,6-penta-O-benzyl-myo-inositol and 2.94 g (9.72 mMol) of triisopropylbenzensulfonyl chloride (TiPSCl) were added to this mixture under stirring and under $N_2$ atmosphere.

After 48 h 10 ml of $H_2O$ were added and the solution was left for 30', after that it was acidified by means of a 0.5 M citric acid solution and extracted with $CHCl_3$. The organic extracts were washed at first with a citric acid solution, then with water, finally dried on $Na_2SO_4$ and the solvent was evaporated under reduced pressure. 4.1 g were obtained of a brown oil which was subsequently purified on a chromatographic column of silica gel (Merck n. 7734). The elution was carried out with the following gradient; chloroform, chloroform-methanol 96:4, chloroform-methanol 85:15.

Obtained were 1.767 g (1.48 mMol) of an oil with a yield of 61%.

Analysis: $C_{72}H_{105}O_{10}PS$ (C,H).

13.5    1-O-(2,3-DITETRADECYLOXYPROPYL-PHOSPHOTHIOLYL)-MYO-INOSITOL.

5 ml of ethylmercaptan and 1.1 ml of boron trifluoride etherate were added to a solution of 286 mg (0.24 mMol) of 1-O-(2,3-ditetradecyloxypropyl-phosphothiolyl)-2,3,4,5,6-penta-O-benzyl-myo-inositol in 5 ml of anhydrous $CHCl_3$ under stirring and under $N_2$ atmosphere. The solution was maintained at room temperature for 1 h, then 5 ml of $H_2O$ were added and the mixture was washed with ether, the aqueous phase was collected and evaporated under reduced pressure while maintaining the water temperature at 25° C.

The white precipitate formed was filtered, washed with water and dried under vacuum at room temperature. Obtained were 46 mg (0.062 mMol) of a white solid (yield 26%).

Analysis: $C_{37}H_{75}O_{10}PS$ (C,H).

EXAMPLE 14

14.1    1-BENZYLTHIO-2,3-DIDODECYLOXY-PROPYLEN GLYCOL.

A suspension consisting of 1.770 g of potassium hydroxide and 1.110 g (5.61 mMol) of 1-benzylthio-2,3-propylen glycol in 60 ml of xylene was brought to reflux under vigorous stirring. After 1 h a solution of 1.826% (6.9 mMol) of dodecylmethansulphonate in 15 ml of xylene were added. The mixture was left under reflux for 4 h, and it was diluted with diethyl ether. Then it was washed with water until reaching washing water neutrality. The organic extracts were dried on $Na_2SO_4$ and the solvent was evaporated under reduced pressure. Obtained were 1.650 g of a very thick pale yellow oil which was purified by silica gel chromatography using as the eluent a mixture of hexane / diethyl ether 95:5 Obtained were 1.095 g of product. The yield was 36.5%

Analysis: $C_{34}H_{62}O_2S$ (C,H).

14.2    2,3-DIDODECYLOXY-1-MERCAPTO-2,3-PROPYLEN GLYCOL

A solution consisting of 75 ml of butanol and 802 mg (1.5 mMol) 1-benzylthio-2,3-didodecyloxy-2,3-propylen-glycol was brought to reflux, then 1.281 g of sodium were added; the mixture was left under reflux until sodium complete dissolution.

Afterwards the solution was cooled to room temperature and diluted with 80 ml of $CHCl_3$; the organic phase was washed with a 1 N citric acid solution until reaching an acid pH then with water until reaching washing water neutrality. The organic extracts were dried on $Na_2SO_4$ and the solvent was evaporated under reduced pressure. Obtained were 333 mE (0.75 mMol) of an oil with a yield of 50%.

Analysis: $C_{27}H_{56}O_2S$ (C,H).

14.3    ETHYL 2,3-DIDODECYLOXYPROPYL-PHOSPHOTHIOLATE.

4.4 ml of n-BuLi (1.6 M) in hexane were added to a solution of 3.108 g (7 mMol) of 2,3-didodecyloxy-1-mercapto-2,3-propylen glycol in 10 ml of anhydrous THF under $N_2$ atmosphere; the solution was stirred for 30' and during this time the formation of a white precipitate was observed. 1.2 g (7 mMol) of diethylchlorophosphate were added; after 1 h, 5 ml of water were added and the solution was extracted with diethyl ether. The ethereal extracts were dried on $Na_2SO_4$ and the solvent was evaporated under reduced pressure obtaining a colourless oil which was purified on a silica gel chromatographic column using as the eluent a mixture of hexane / ethyl acetate 6:4. Obtained were 2.765 g (4.76 mMol) of an oil with a yield of 68%.

Analysis: $C_{31}H_{65}O_5PS$ (C,H).

14.4 1-O- (2,3-DIDODECYLOXYPROPYLPHOS-PHOTHIOLYL)    -2,3,4,5,6-PENTA-O-BENZYL-MYO-INOSITOL 1 ml (7.3 mMol) of trimethylsilyl bromide was added to a solution of 1.411 g (2.43 mMol) of ethyl-2,3-didodecyloxypropylphosphothiolate in 1 ml anhydrous $CH_2Cl_2$ under stirring and under $N_2$ atmosphere.

The mixture obtained was maintained for 6 h at room temperature, afterwards the solvent was evaporated under reduced pressure and a mixture composed by 4 ml of anhydrous pyridine and 3 ml of anhydrous $CHCl_3$ was added.

2 ml (14.4 mMol) of triethylamine, 1.4 g (2.2 mMol) of D,L-2,3,4,5,6-penta-O-benzyl-myo-inositol and 2.94 g (9.72 mMol) of triisopropylbenzensulfonyl chloride (TiPSCl) were added to this mixture under stirring and under $N_2$ atmosphere.

After 48 h 10 ml of $H_2O$ were added and the solution was left for 30', after that it was acidified by means of a 0.5 M citric acid solution and extracted with $CHCl_3$. The organic extracts were washed at first with a citric acid solution, then with water, finally dried on $Na_2SO_4$ and the solvent was evaporated under reduced pressure. 3.96 g of a brown oil were obtained which was subsequently purified on a chromatographic column of silica gel (Merck n. 7734). The elution was carried out with the following gradient; chloroform, chloroform-methanol 96:4, chloroform-methanol 85:15.

Obtained were 1.627 g (1.43 mMol) of an oil with a yield of 59%.

Analysis: $C_{68}H_{97}O_{10}PS$ (C,H).

14.5    1-O-(2,3-DIDODECYLOXYPROPYLPHOS-PHOTHIOLYL)-MYO-INOSITOL.

5 ml of ethylmercaptan and 1.1 ml of boron trifluoride etherate were added to a solution of 273 mg (0.24 mMol) of 1-O-(2,3-didodecyloxypropyl-phosphothiolyl)-2,3,4,5,6-penta-O-benzyl-myo-inositol in 5 ml of anhydrous $CHCl_3$, under stirring and under $N_2$ atmosphere. The solution was maintained at room temperature for 1 h, then 5 ml of $H_2O$ were added and the mixture was washed with ether, the aqueous phase was collected and evaporated under reduced pressure while maintaining the water temperature at 25° C.

The white precipitate formed was filtered, washed with water and dried under vacuum at room temperature. Obtained were 51 mg (0.075 mMol) of a white solid (yield 31%).

Analysis: $C_{33}H_{67}O_{10}PS$ (C,H).

EXAMPLE 15

15.1    1-BENZYLTHIO-2,3-DIOCTYLOXYPRO-PYLEN GLYCOL.

A suspension consisting of 1.770 g of potassium hydroxide and 1.110 g (5.61 mMol) of 1-benzylthio-2,3-propylen glycol in 60 ml of xylene was brought to reflux under vigorous stirring. After 1 h a solution of 1.440 g (6.9 mMol) of octylmethansulfonate in 15 ml of xylene was added drop by drop. The mixture was left under reflux for 4 h, then it was diluted with diethyl ether. Said mixture was washed with water until reaching washing water neutrality. The organic extracts were dried on $Na_2SO_4$ and the solvent was evaporated under reduced pressure. Obtained were 1.263 g of a very thick pale yellow oil which was purified by silica gel chromatography using as the eluent a mixture of hexane / diethyl ether 95:5. Obtained were 0.870 g of product. The yield was 36.6%.

Analysis: $C_{26}H_{46}O_2S$ (C,H).

15.2 2,3-DIOCTYLOXY-1-MERCAPTO-2,3-PROPYLEN GLYCOL

A solution consisting of 75 ml of butanol and 634 mg (1.5 mMol) of 1-benzylthio-2,3-dioctyloxy-2,3-propylen-glycol was brought to reflux, then 941 g of sodium were added; the mixture was left under reflux until sodium complete dissolution.

Afterwards the solution was cooled to room temperature and diluted with 80 ml of $CHCl_3$; the organic phase was washed with a 1 N citric acid solution until reaching an acid pH then with water until reaching washing water neutrality. The organic extracts were dried on $Na_2SO_4$ and the solvent was evaporated under reduced pressure. Obtained were 239 mg (0.72 mMol) of an oil with a yield of 48%.

Analysis: $C_{19}H_{40}O_2S$ (C,H).

15.3 ETHYL 2,3-DIOCTYLOXYPROPYLPHOSPHOTHIOLATE.

4.4 ml of n-BuLi (1.6 M) in hexane were added to a solution of 2.328 g (7 mMol) of 2,3-dioctyloxy-1-mercapto-2,3-propylen glycol in 10 ml of anhydrous THF under $N_2$ atmosphere; the solution was stirred for 30' and during this time the formation of a precipitate was observed. 1.2 g (7 mMol) of diethylchlorophosphate were added; after 1 h, 5 ml of water were added and said mixture was extracted with diethyl ether. The ethereal extracts were dried on $Na_2SO_4$ and the solvent was evaporated under reduced pressure, thereby obtaining a colourless oil which was purified on a silica gel chromatographic column using as the eluent a mixture of hexane / ethyl acetate 6:4. Obtained were 2.067 g (4.41 mMol) of an oil with a yield of 63%.

Analysis: $C_{23}H_{49}O_5PS$ (C,H).

15.4 1-O-(2,3-DIOCTYLOXYPROPYLPHOSPHOTHIOLYL)-2,3,4,5,6-PENTA-O-BENZYL-MYO-INOSITOL 1 ml (7.3 mMol) of trimethylsilyl bromide was added to a solution of 1.139 g (2.43 mMol) of ethyl-2,3-dioctyloxypropylphosphothiolate in 1 ml anhydrous $CH_2Cl_2$ under stirring and under $N_2$ atmosphere.

The mixture obtained was maintained for 6 h at room temperature, afterwards the solvent was evaporated under reduced pressure and a mixture composed by 4 ml of anhydrous pyridine and 3 ml of anhydrous $CHCl_3$ was added.

2 ml (14.4 mMol) of triethylamine, 1.4 g (2.2 mMol) of D,L-2,3,4,5,6-penta-O-benzyl-myo-inositol and 2.94 g (9.72 mMol) of triisopropylbenzensulfonyl chloride (TiPSCl) were added to this mixture under stirring and under $N_2$ atmosphere.

After 48 h 10 ml of $H_2O$ were added and the solution was left for 30', after that it was acidified by means of a 0.5 M citric acid solution and extracted with $CHCl_3$. The organic extracts were washed at first with a citric acid solution, then with water, finally dried on $Na_2SO_4$ and the solvent was evaporated under reduced pressure. 3.01 g of a brown oil were obtained which was subsequently purified on a chromatographic column of silica gel (Merck n. 7734). The elution was carried out with the following gradient; chloroform, chloroform-methanol 96:4, chloroform-methanol 85:15.

Obtained were 1.169 g (1.14 mMol) of an oil with a yield of 47%.

Analysis: $C_{60}H_{81}O_{10}PS$ (C,H).

15.5 1-O-(2,3-DIOCTYLOXYPROPYLPHOSPHOTHIOLYL)-MYO-INOSITOL.

5 ml of ethylmercaptan and 1.1 ml of boron trifluoride etherate were added to a solution of 246 mg (0.24 mMol) of 1-O-(2,3-dioctyloxypropyl-phosphothiolyl)-2,3,4,5,6-penta-O-benzyl-myoinositol in 5 ml of anhydrous $CHCl_3$, under stirring and under $N_2$ atmosphere. The solution was maintained at room temperature for 1 h, then 5 ml of $H_2O$ were added and the mixture was washed with ether, the aqueous phase was collected and evaporated under reduced pressure while maintaining the water temperature at 25° C.

The white precipitate formed was filtered, washed with water and dried under vacuum at room temperature. Obtained were 39 mg (0.067 mMol) of a white solid (yield 28%).

Analysis: $C_{25}H_{51}O_{10}PS$ (C,H).

EXAMPLE 16

16.1 BIS-BENZOTRIAZOLYLPHENILPHOSPHATE

A solution of phenyldichlorophosphate (1.5 ml, 10 mMol) in 10 ml of anhydrous dioxane was added drop by drop to a solution of hydroxybenzotriazole (2.753 g, 20 mMol) previously dried on $P_2O_5$ under vacuum at 60° C. for three days, and anhydrous pyridine (1.62 ml 20.06 mMol) in 40 ml of anhydrous dioxane under nitrogen atmosphere. The mixture was stirred for 1 h at room temperature, and filtered, the filtrate thus obtained was stored at $-18°$ C.

16.2 1-O-OCTADECYLPHENYLPHOSPHATE-2,3,4,5,6-PENTA-O-BENZYL-MYO-INOSITOL.

A solution of bisbenzotriazolylphosphate in dioxane (0.2 M, 17.6 ml, 3.53 mmol) was quickly dropped onto 2 g (0.317 mMol) of 2,3,4,5,6-penta-O-benzyl-myo-inositol under nitrogen atmosphere and under stirring. The mixture obtained was left at room temperature for 1 h, then 0.78 g (2.9 mMol) of octadecanol and 1.26 ml (15.85 mMol) of 1 methylimidazol were added. The mixture was stirred at room temperature for 20 h. The reaction was followed by TLC, using as the eluent $Et_2O$ / petroleum ether 1:1.

The reaction was interrupted by adding 5 ml of phosphate buffer (pH=7) and by diluting with $CH_2Cl_2$. The mixture was transferred into a separatory funnel and the organic phase was washed at first with water, then with phosphate buffer and finally with water again. The extracts were collected and dried on $Na_2SO_4$, the solvent was evaporated, thereby recovering 3.1 g of a pale yellow clear oil which was purified by chromatography on silica gel (Merck n. 7734) which was previously deactivated with 5% by weight of water, using as the eluent the mixture hexane / ethylacetate 85:15 (Rf 0.3).

Obtained were 2.14 g (2.06 mMol) of a clear oil (yield 71%).

Analysis: $C_{65}H_{83}O_9P$ (C,H).

$^1$H-NMR (200 MHz, $CDCl_3$): δ0.82 (t,3H), 1.25(m,30H), 1.55(m,2H), 3.5(t, 2H), 3.53(m, 4H), 4.04(m, 2H), 4.78(m, 10H), 7.26(m, 3OH) ppm.

16.3 1-O-OCTADECYLPHOSPHATE-2,3,4,5,6-PENTA-O-BENZYL-MYO-INOSITOL 2.28 ml (2.5 mMol, 1.1 M in THF) of tetrabutyl ammonium fluoride (TBAF) were added to a solution of 1.319 g (1.27 mMol) of 1-octadecylphenylphosphate-2,3,4,5% 6-penta-O-benzyl-myo-inositol in 31 ml of anhydrous tetrahydrofuran, under stirring and under nitrogen atmosphere. The mixture was left until the starting product was completely absent (about 3 h), then water was added to the solution, and the mixture thus obtained was transferred into a separatory funnel, where it was extracted three times with $CH_2Cl_2$, the organic extracts were collected, dried on $Na_2SO_4$ and the solvent was evaporated, thereby giving 1.562 g of a pale yellow clear oil which was purified by chromatography on silica gel (Merck n. 7734) previously washed with $H^+$ and deactivated with 10% by weight of water.

Obtained were 850 mg (0.88 mMol) of a clear oil (yield 70%).

Analysis: $C_{59}H_{79}O_9P$ (C,H).

$^1$H-NMR (200 MHz, $CDCl_3$): $\delta$0.82 (t, 3H), 1.25(m, 30H), 1.55(m, 2H), 3.5(t, 2H), 3.53(m, 4H), 4.04 (m, 2H), 4.78(m, 10H), 7.26(m, 25H) ppm.

16.4  1-O-OCTADECYLPHOSPHATE-MYO-INOSITOL.

12.8 ml of ethylmercaptan and 2.56 ml of boron trifluoride etherate were added to a solution of 630 mg (0.65 mMol) of 1-O-octadecylphosphate-2,3,4,5,6-penta-O-benzyl-myo-inositol in 10 ml of anhydrous $CH_2Cl_2$, under stirring and under nitrogen atmosphere. The mixture was left at room temperature for 1 h, after that it was diluted with water and transferred into a separatory funnel. The aqueous phase was washed repeatedly with ethyl ether until ehylmercaptan complete remotion and it was divided into two portion, the first one being clear, and the second one containing a white flocculent precipitate. This latter portion was congealed and lyophilized. Obtained were 330 mE (0.64 mMol) of a pure final product (a white pearly solid) in quantitative yield.

Analysis: $C_{24}H_{49}O_9P$ (C,H).

$^1$H-NMR (200 MHz, DMSO-$d_6$/$CDCl_2CDCl_2$): $\delta$0.83 (t,3H), 1.25(m, 32H), 1.55(m. 2H), 2.95(t, 2H), 3.12 (dd, $^1$H), 3-37(t, $^1$H), 3.53(t, 1H), 3.85(m, 2H) ppm.

EXAMPLE 17

17.1  1-O-HEXADECYLPHENYLPHOSPHATE-2,3,4,5,6-PENTA-O-BENZYL-MYO-INOSITOL.

A solution of bis-benzotriazolylphenylphosphate (as prepared in example 16) in dioxane (0.2 M, 17.6 ml, 3.53 mmol) was quickly dropped onto 2 g (0.317 mMol) of 2,3,4,5,6-penta-O-benzyl-myoinositol under nitrogen atmosphere and under stirring. The mixture obtained was left at room temperature for 1 h, then 0.702 g (2.9 mMol) of hexadecanol and 1.26 ml (15.85 mMol) of 1-methylimidazol were added. The mixture was stirred at room temperature for 20 h. The reaction was followed by TLC, using as the eluent $Et_2O$ / petroleum ether 1:1.

The reaction was interrupted by adding 5 ml of phosphate buffer (pH=7) and by diluting with $CH_2Cl_2$. The mixture was transferred into a separatory funnel and the organic phase was washed at first with water, then with phosphate buffer and finally with water again. The extracts were collected and dried on $Na_2SO_4$, the solvent was evaporated under reduced pressure, thereby recovering 2.8 g of a pale yellow clear oil which was purified by chromatography on silica gel (Merck n. 7734), which was previously deactivated with 5% by weight of water, using as the eluent the mixture hexane / ethylacetate 85:15 (Rf 0.3).

Obtained were 2.05 g (2.03 mMol) of a clear oil (yield 70%).

Analysis: $C_{63}H_{79}O_9P$ (C,H).

$^1$H-NMR (200 MHz, $CDCl_3$): $\delta$0.82 (t,3H), 1.25(m,26H), 1.55(m,2H), 3.5(t, 2H), 3.53(m, 4H), 4.04(m, 2H), 4.78(m, 10H), 7.26(m, 30H) ppm.

17.2  1-O-HEXADECYLPHOSPHATE-2,3,4,5,6-PENTA-O-BENZYL-MYO-INOSITOL 2.28 ml (2.5 mMol, 1.1M in THF) of tetrabutyl ammonium fluoride (TBAF) were added to a solution of 1.29 g (1.27 mMol) of 1-hexadecylphenylphosphate-2,3,4,5,6-penta-O-benzyl-myo-inositol in 31 ml of anhydrous tetrahydrofuran, under stirring and under nitrogen atmosphere. The mixture was left until the starting product was completely absent (about 3 h), then water was added to the solution, and the mixture thus obtained was transferred into a separatory funnel where it was extracted three times with $CH_2Cl_2$, and the organic extracts were collected, dried on $Na_2SO_4$ and the solvent was evaporated, thereby giving 1.6 g of a pale yellow clear oil which was purified by chromatography on silica gel (Merck n. 7734) previously washed with $H^+$ and deactivated with 10% by weight of water.

Obtained were 822 mg (0.88 mMol) of a clear oil (yield 69%).

Analysis: $C_{57}H_{75}O_9P$ (C,H).

$^1$H-NMR (200 MHz, $CDCl_3$): $\delta$ 0.82 (t, 3H), 1.25(m, 26H), 1.55(m, 2H), 3.5(t, 2H), 3.53(m, 4H), 4.04(m, 2H), 4.78(m, 10H), 7.26(m, 25H) ppm.

17.3  1-O-HEXADECYLPHOSPHATE-MYO-INOSITOL.

12.8 ml of ethylmercaptan and 2.56 ml of boron trifluoride etherate were added to a solution of 607 mg (0.65 mMol) of 1-O-hexadecylphosphate-2,3,4,5,6-penta-O-benzyl-myo-inositol in 10 ml of anhydrous $CH_2Cl_2$, under stirring and under nitrogen atmosphere. The mixture was left at room temperature for 1 h, after that it was diluted with water and transferred into a separatory funnel. The aqueous phase was washed repeatedly with ethyl ether until ethylmercaptan complete remotion and it was divided into two portion, the first one being clear, and the second one containing a white flocculent precipitate. This latter portion was congealed and lyophilized. Obtained were 305 mg (0.63 mMol) of a pure final product (a white pearly solid) in quantitative yield.

Analysis: $C_{22}H_{45}O_9P$ (C,H).

$^1$H-NMR (200 MHz, DMSO-$d_6$/$CDCl_2CDCl_2$): $\delta$0.83 (t,3H), 1.25(m, 28H), 1.55(m, 2H), 2.95(t, 2H), 3.12 (dd, 1H), 3.37(t, 1H), 3.53(t, $^1$H), 3.85(m, 2H) ppm.

EXAMPLE 18

18.1 1-O-TETRADECYLPHENYLPHOSPHATE-2,3,4,5,6-PENTA-O-BENZYL-MYO-INOSITOL.

A solution of bis-benzotriazolylphenylphosphate (as prepared in example 16) in dioxane (0.2 M, 17.6 ml, 3.53 mmol) was quickly dropped onto 2 g (0.317 mMol) of 2,3,4,5,6-penta-O-benzyl-myo-inositol under nitrogen atmosphere and under stirring. The mixture obtained was left at room temperature for 1 h, then 0.621 g (2.9 mMol) of tetradecanol and 1.26 ml (15.85 mMol) of 1-methylimidazol were added. The mixture was stirred at room temperature for 20 h. The reaction was followed by using TLC and by using as the eluent $Et_2O$ / petroleum ether 1:1.

The reaction was interrupted by adding 5 ml of phosphate buffer (pH=7) and by diluting with $CH_2Cl_2$. The mixture was transferred into a separatory funnel and the organic phase was washed at first with water, then with phosphate buffer and finally with water again. The extracts were collected and dried on $Na_2SO_4$, the solvent was evaporated under reduced pressure, thereby recovering 2.6 g of a pale yellow clear oil which was purified by chromatography on silica gel (Merck n. 7734) which was previously deactivated with 5% by weight of water, using as the eluent the mixture hexane / ethylacetate 85:15 (Rf 0.3).

Obtained were 2.08 g (2.12 mMol) of a clear oil (yield 73%).

Analysis: $C_{61}H_{75}O_9P$ (C,H).

$^1$H-NMR (200 MHz, $CDCl_3$): δ0.82 (t,BH), 1.25(m,22H), 1.55(m,2H), 3.5(t, 2H), 3.53(m, 4H), 4.04(m, 2H), 4.78(m, 10H), 7.26(m, 30H) ppm.

18.2 1-O-TETRADECYLPHOSPHATE-2,3,4,5,6-PENTA-O-BENZYL-MYO-INOSITOL 2.28 ml (2.5 mMol, 1.1M in THF) of tetrabutyl ammonium fluoride (TBAF) were added to a solution of 1.25 g (1.27 mMol) of 1-tetradecylphenylphosphate-2,3,4,5,6-penta-O-benzyl-myo-inositol in 31 ml of anhydrous tetrahydrofuran under stirring and under nitrogen atmosphere. The mixture was left until the starting product was completely absent (about 3 h), then water was added to the solution, and the mixture thus obtained was transferred into a separatory funnel where it was extracted three times with $CH_2Cl_2$; the organic extracts were collected, dried on $Na_2SO_4$ and the solvent was evaporated, thereby giving 1.56 g of a pale yellow clear oil which was purified by chromatography on silica gel (Merck n. 7734) previously washed with $H^+$ and deactivated with 10% by weight of water.

Obtained were 782 mg (0.86 mMol) of a clear oil (yield 68%).

Analysis: $C_{55}H_{71}O_9P$ (C,H).

$^1$H-NMR (200 MHz, $CDCl_3$): δ0.82 (t, 3H), 1.25(m, 22H), 1.55(m, 2H), 3.5(t, 2H), 3.53(m, 4H), 4.04(m, 2H), 4.78(m, 10H), 7.26(m, 25H) ppm.

18.3 1-O-TETRADECYLPHOSPHATE-MYO-INOSITOL.

12.8 ml of ethylmercaptan and 2.56 ml of boron trifluoride etherate were added to a solution of 589 mE (0.65 mMol) of 1-O-octadecylphosphate-2,3,4,5,6-penta-O-benzyl-myo-inositol in 10 ml of anhydrous $CH_2Cl_2$, under stirring and under nitrogen atmosphere. ? he mixture was left at room temperature for 1 h, after that it was diluted with water and transferred into a separatory funnel. The aqueous phase was washed repeatedly with ethyl ether until ethylmercaptan complete remotion and it was divided into two portion, the first one being clear, and the second one containing a white very flocculent precipitate. This latter portion was congealed and lyophilized. Obtained were 292 mg (0.64 mMol) of a pure final product (a white pearly solid) in quantitative yield.

Analysis: $C_{20}H_{41}O_9P$ (C,H).

$^1$H-NMR (200 MHz, DMSO-$d_6$/$CDCl_2CDCl_2$): δ0.83 (t,3H), 1.25(m, 24H), 1.55(m, 2H), 2.95(t, 2H), 3.12 (dd, $^1$H), 3.37(t, 1H), 3.53(t, $^1$H), 3.85(m, 2H) ppm.

PHARMACOLOGICAL TESTS

The following experiments were carried out with the compounds prepared in the Examples 1–5 above mentioned in order to evaluate their ability to inhibit the enzymatic activity of phosphatidylinositol-specific phospholipase C (PLC).

The test were carried out according to the following operations.

1. Preparation of phosphatidylinositol-specific phospholipase C enzyme from human platelets.

As the starting material human plasma enriched with human platelets was used.

Platelets were precipitated from plasma by centrifugation at 0°–4° C. for 30 minutes at 2,500×g. The platelets precipitate was washed twice by using a buffer "A" Hepes pH 7 (137 mM NaCl, 20 mM Hepes; 1.0 mM EGTA; 5 mM glucose) and successively recovered by using buffer "B" Hepes (10 mM Hepes, pH 7).

The platelets were sonicated and centrifuged at 3,200×g for 20 minutes at 0–4° C. The surnatant consisting of platelets homogenate, was separated and ultracentrifuged at 105,000×g for 1 hour, thereby obtaining two fractions: the soluble one and the particulate one, both containing PLC.

The more active fraction was the soluble one which was successively used for the enzymatic activity test as described in the following item 3.

2. Preparation of phosphatidylinositol substrate.

The substrate marked for PLC, L-3-phosphatidyl [2-$^3$H] inositol, cod. TRK.713, was purchased by Amersham International and it was obtained from the incubation of [2-$^3$H]-myo-inositol with a suitable fraction of purified microsomes coming from adult bovine brain.

The product was purified by HPLC and had the following characteristics: specific activity 20 Ci/mMol (22.6 mCi/mg), radioactivity concentration 50μCi/ml ($2.22 \times 10^6 \times 50/60 = 1.85 \times 10^6$ Bq); the hydroxyl groups 1 and 2 of glycerol resulted esterified with stearic acid and arachidonic acid in 90% of the product.

1 ml of a chloroform solution containing L-phosphatidylinositol (10 mg/ml sigma cod P 25/7 containing mainly stearic acid and arachidonic acid) was taken. After evaporation of the solvent under nitrogen the remaining 10.3 mg of substrate were dissolved in 50 ml of buffer Tris maleate 50 mM (pH 6.5) containing free calcium ions ($CaCl_2$ 1.0 mM) and sodium desoxycholate (0–2 mg per ml). Marked phosphatidylinositol was added to 9 ml of said solution in such an amount that in 300μl of the solution ($2.0 \times 10^{-4}$ M) thus obtained, 130,078±1316 Dpm were recorded. In the resulting solution the molar ratio "cold/hot" was therefore $2 \times 10^4$.

3. Evaluation of the enzymatic activity.

The hydrolysis of phosphatidylinositol was carried out in a medium buffered at pH 6.5 (trismaleate 50 mM, $CaCl_2$ 1.0 mM), in a bath fitted with a thermostat regulated at 37° C., 300μl of enzymatic solution, 300 μl of substrate and buffer or of substrate and buffer+inhibitor, were employed, the whole amounting to a total final volume of 700 μl. The enzymatic concentration of every single sample at pH, temperature and ionic strength already specified, was: $6.16 \times 10^{-4}$ unit/ml of reaction mixture, equal to $14.4 \times 10^{-4}$ unit/ml of enzymatic solution.

In the case of the test carried out without inhibitor, the reaction mixture was incubated at 37° C. for 15 minutes during which the hydrolysis rate kept constant.

The enzymatic activity was then interrupted, by adding 2.0–3.0 ml of a mixture chloroform/methanol/hydrochloric acid (1,000:1,000:24).

In order to determine the inhibitory activity of the compounds of the present invention, said compounds and the enzyme were preincubated for 20 minutes. Successively the substrate was added and the enzymatic reaction was interrupted after 15 minutes. A suitable aliquot of the aqueous phase was utilized for the scintillatot readings.

The results of said tests are reported in the following table 1:

TABLE 1

| EXAMPLE | COMPOUND | M.W. | *IC$_{50}$(M) |
|---|---|---|---|
| 1.3 | $CH_3-(CH_2)_{17}-S-P(=O)(OH)-O-$[inositol] | 528.67 | $\approx 5 \cdot 10^{-5}$ |
| 2.3 | $CH_3-(CH_2)_{15}-S-P(=O)(OH)-O-$[inositol] | 500.57 | $\approx 4 \cdot 10^{-5}$ |
| 3.3 | $CH_3-(CH_2)_{13}-S-P(=O)(OH)-O-$[inositol] | 472.57 | $\approx 10^{-4}$ |
| 4.3 | $CH_3-(CH_2)_{11}-S-P(=O)(OH)-O-$[inositol] | 444.51 | $> 10^{-4}$ |
| 5.3 | $CH_3-(CH_2)_{7}-S-P(=O)(OH)-O-$[inositol] | 388.41 | $>> 10^{-4}$ |

*IC$_{50}$ Inhibitor concentration inhibiting 50% of the enzyme

Analogous results were achieved in pharmacological tests carried out with the compounds prepared according to Examples from 6 to 18.

ANTITUMORAL ACTIVITY

The compound described in example 1.3 and named 309 bis was tested to evaluate the "in vitro" antitumoral activity according to the following method:

Cell cultures. K562 erythroleukaemia cell line was obtained from ATCC (Rockville, Md., USA). Cell culture media and plastic were from Flow (U.K.). Cells were grown in RPMI 1640 medium supplemented with 10% (v/v) heat-inactivated foetal calf serum, 2mM L-glutamine, 2.0 g.1$^{-1}$ bicarbonate, and 10 mM Hepes (4-(2-hydroxyethyl)-1-piperazine ethanesulphonic acid) in humidified atmosphere with 5% (v/v) $CO_2$ at 37° C. Coltures were performed without the addition of any antibiotics, and were routinely checked for the presence of Mycoplasma infection.

Toxicity assay. Cells were washed and suspended to the final concentration of 10$^6$ml$^{-1}$ in a medium containing 5% (v/v) FCS. The chemical compounds under evaluation were diluted from a 2 mM stock solution containing 5% (v/v) FCS and 0.2% (v/v) dimethylsulphoxide (DMSO, FCS and medium were added in sequence to facilitate solubility); when necessary, solutions were treated with short sonical pulses. 0.2% DMSO was added to controls. Compounds were added to a final concentration ranging from 10$^{-6}$ to 10$^{-3}$ M, and kept in a humidified atmosphere with 5% (v/v)

$CO_2$ at 37° C. Cell death was visualized by adding 50 mM propidium iodide (Sigma, USA) to 100 ml aliquots of unfixed cells. The 560–580 nm fluorescence of the death cells, excited at 490–495 nm, was monitored on a FACS-analizer flow cytofluorometer (Becton Dickinson, Calif., USA) using a Consort 30 programme. About 10,000 events were collected for each point, at 0.5,1,2,4, and 24 hours. The antitumoral activity results of said compound ape reported in the diagram of FIG. 1, where in ordinate axis the % toxicity, namely the percentage of killed cells is reported, while in abscissa axis the contact hours of the compound 309 bis with the tumoral cells are reported.

As it clearly results from said diagram the compound 309 bis shows antitumoral activity on erythroleukaemic cells even at a concentration $10^{-5}$ M, and said antitumoral activity reaches its maximum (almost 100% of killed cells) when the concentration of the compound 309 bis ranges from $10^{-3} - 3 \times 10^{-3}$ M.

Thanks to their inhibitory activity towards PLC, the compounds of the invention can be used in admixture with pharmaceutically acceptable diluents or excipients for preparing pharmaceutical compositions suitable for treating tumoral, thrombotic and inflammatory type pathologies.

The method for the treatment of said pathologies comprises administering orally or parenterally an effective amount of the compounds of the invention.

We claim:

1. Phosphatidylinositol analogues, inhibitors of phosphatidylinositol-specific phospholipase C, having the general formula (I)

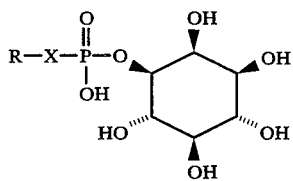
(I)

wherein X is S or O, and R has one of the following meanings:

1) a branched or linear alkyl radical selected from the group consisting of octyl, tetradecyl, hexadecyl, octadecyl, and eicosyl;
2) an arylalkyl radical selected from the group consisting of benzyl, phenylethyl, naphthylethyl, phenylpropyl, and phenylhexyl;
3) 2,3 diacyloxypropyl:

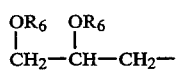

wherein $R_6$ is a saturated or unsaturated acyl radical selected from the group consisting of oleyl, linoleyl, linolenyl, myristoyl, and lauroyl;

4) 2,3 dialkyloxypropyl:

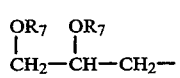

wherein $R_7$ is a saturated or unsaturated alkyl radical selected from the group consisting of stearyl, palmityl, oleyl, myristyl, and cetyl;

5) 2,3 alkylacyloxypropyl

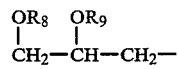

wherein $R_8$ is a saturated or unsaturated alkyl radical selected from the group consisting of stearyl, palmityl, oleyl, myristyl, and cetyl and $R_9$ is acetyl;

6) an alkyl radical containing a carbonyl group of formula:

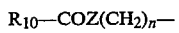

wherein $R_{10}$ has the same meaning as R at item 1, Z=O, NH, and n ranges from 2 to 6;

7) an alkyl radical containing a carbonyl group of formula:

wherein $R_{10}$ has the same meaning as R at item 5, Y=O, NH, S and m ranges from 1 to 6.

2. A process for preparing phosphatidylinositol analogue inhibitors of phosphatidylinositol-specific phospholipase C having the following general formula (I):

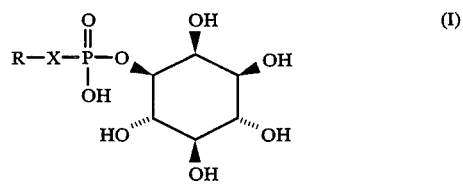
(I)

wherein X is S or O, and R has one of the following meanings:

1) a branched or linear alkyl radical selected from the group consisting of octyl, tetradecyl, hexadecyl, octadecyl, and eicosyl;
2) an arylalkyl radical selected from the group consisting of benzyl, phenylethyl, naphthylethyl, phenylpropyl, and phenylhexyl;
3) 2,3 diacyloxypropyl:

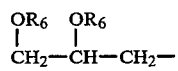

wherein $R_6$ is a saturated or unsaturated acyl radical selected from the group consisting of oleyl, linoleyl, linolenyl, myristoyl, and lauroyl;

4) 2,3 dialkyloxypropyl:

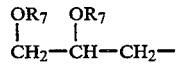

wherein $R_7$ is a saturated or unsaturated alkyl radical selected from the group consisting of stearyl, palmityl, oleyl, myristyl, and cetyl;

5) 2,3 alkylacyloxypropyl

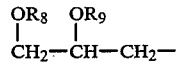

wherein $R_8$ is a saturated or unsaturated alkyl radical selected from the group consisting of stearyl, palmityl, oleyl, myristyl, and cetyl and $R_9$ is acetyl;

6) an alkyl radical containing a carbonyl group of formula:

$$R_{10}\text{—COZ(CH}_2)_n\text{—}$$

wherein $R_{10}$ has the same meaning as R at item 1, Z=O, NH, and n ranges from 2 to 6;

7) an alkyl radical containing a carbonyl group of formula:

$$R_{10}\text{—YCO(CH}_2)_m\text{—}$$

wherein $R_{10}$ has the same meaning as R at item 5, Y=O, NH, S and m ranges from 1 to 6; wherein when X=S, said process comprises:

(a) transesterifying by treatment with trimethylsilylbromide a diethylphosphothiolate having the general formula:

$$\underset{\underset{\text{OEt}}{|}}{\overset{\overset{\text{O}}{\|}}{R\text{—S—P—OEt}}} \quad (II)$$

(b) treating the transesterified product of step (a) with myoinositol protected at hydroxyl groups 2, 3, 4, 5 and 6 in the presence of a condensing agent; and (c) removing the protecting groups of the compound produced in step (b) and thereby restoring the hydroxyl groups 2, 3, 4, 5 and 6;

and wherein when X=O, said process comprises:

(a) transesterifying by treatment with trimethylsilylbromide a phosphoric triester having the formula:

$$\underset{\underset{\text{OEt}}{|}}{\overset{\overset{\text{O}}{\|}}{R\text{—O—P—OEt}}}$$

(b) treating the transesterified product of step (a) with myoinositol protected at hydroxyl groups 2, 3, 4, 5 and (c) removing the protecting groups of the compound produced in step (b) and thereby restoring the hydroxyl groups 2, 3, 4, 5 and 6.

3. The process according to claim 2 wherein said transesterification is carried out in $CH_2Cl_2$ under inert gas atmosphere at room temperature and by using a molar ratio of trimethylsilylbromide : phosphothiolate comprised between 2.5 and 4.5.

4. The process according to claim 2, wherein said myoinositol is protected at said hydroxyl groups with protecting groups selected from benzyl, allyl, trialkylsilyl, alkylarylsilyl, tetrahydropyranyl, acetonitril, cyclohexylidene, acetyl, propanoyl, butirryl, and pentanoyl.

5. The process according to claim 2, wherein said treatment with myoinositol is carried out in pyridine and triethylamine and optionally $CHCl_3$ ambient under inert gas atmosphere, at room temperature and by using a molar ratio myoinositol:phosphothiolate comprised between 0.8 and 2.

6. The process according to claim 2, wherein said remotion of the benzyl protecting groups, in order to restore the hydroxyl groups 2,3,4,5 and 6 is carried out in $CHCl_3$, under inert gas atmosphere, at room temperature, by using a quantity of from to 25 ml of ethylmercaptan and of from 3 to 5 ml of boron trifluoride etherate per mMol of myo-inositol derivative.

* * * * *